(12) United States Patent
Tracey et al.

(10) Patent No.: US 9,981,978 B2
(45) Date of Patent: May 29, 2018

(54) PREPARATION OF SATURATED KETONE MORPHINAN COMPOUNDS BY CATALYTIC ISOMERISATION

(71) Applicant: Cambrex Charles City, Inc., Charles City, IA (US)

(72) Inventors: Michael Tracey, Charles City, IA (US); Pär Holmberg, Charles City, IA (US); Belén Lindberg Martín Matute, Stockholm (SE); Antonio Bermejo Gómez, Sundbyberg (SE); Jan-Erling Bäckvall, Stocksund (SE)

(73) Assignee: Cambrex Charles City, Inc., Charles City, IA (US)

( * ) Notice: Subject to any disclaimer, the term of this patent is extended or adjusted under 35 U.S.C. 154(b) by 171 days.

(21) Appl. No.: 14/906,776

(22) PCT Filed: Jul. 23, 2014

(86) PCT No.: PCT/GB2014/052250
§ 371 (c)(1),
(2) Date: Jan. 21, 2016

(87) PCT Pub. No.: WO2015/011474
PCT Pub. Date: Jan. 29, 2015

(65) Prior Publication Data
US 2016/0168159 A1   Jun. 16, 2016

(30) Foreign Application Priority Data
Jul. 24, 2013  (GB) .................................. 1313211.3

(51) Int. Cl.
*C07D 489/02* (2006.01)
*A61K 31/485* (2006.01)
*B01J 31/18* (2006.01)

(52) U.S. Cl.
CPC ........ *C07D 489/02* (2013.01); *B01J 31/1805* (2013.01); *B01J 2231/645* (2013.01); *B01J 2531/822* (2013.01)

(58) Field of Classification Search
CPC ............................ A61K 31/485; C07D 489/02
USPC ........................................... 514/282; 546/45
See application file for complete search history.

(56) References Cited

U.S. PATENT DOCUMENTS

| | | | |
|---|---|---|---|
| 5,847,142 | A | 12/1998 | Mudryk et al. |
| 7,129,248 | B2 | 10/2006 | Chapman et al. |
| 7,399,859 | B1 | 7/2008 | Kouznetsov |
| 7,550,592 | B2 | 6/2009 | Lorimer et al. |
| 7,674,800 | B2 | 3/2010 | Chapman et al. |
| 7,683,072 | B2 | 3/2010 | Chapman et al. |
| 7,851,482 | B2 | 12/2010 | Dung et al. |
| 2005/0124811 | A1 | 6/2005 | Wang et al. |
| 2007/0072889 | A1 | 3/2007 | Hagen et al. |
| 2007/0179169 | A1 | 8/2007 | Chapman et al. |
| 2008/0188661 | A1 | 8/2008 | Kouznetsov |
| 2008/0312442 | A1* | 12/2008 | Buehler ............... A61K 31/485 546/45 |
| 2009/0022798 | A1 | 1/2009 | Rosenberg et al. |
| 2010/0261904 | A1 | 10/2010 | Wang et al. |
| 2010/0261906 | A1 | 10/2010 | Haar, Jr. et al. |
| 2010/0261907 | A1 | 10/2010 | Wang et al. |
| 2011/0071016 | A1 | 3/2011 | Gindelberger |

FOREIGN PATENT DOCUMENTS

| | | |
|---|---|---|
| DE | 365683 C | 12/1922 |
| DE | 380919 C | 9/1923 |
| DE | 623821 C | 8/1934 |
| WO | 9805667 A1 | 2/1998 |
| WO | 2006104656 A1 | 10/2006 |
| WO | 2008070658 A1 | 6/2008 |
| WO | 2012003468 A1 | 1/2012 |

OTHER PUBLICATIONS

Ahlsten et al., "Rhodium-catalysed isomeration of allylic alcohols in water at ambient temperature", Green Chem., 2010, 12 (9), 1628-1633.
Cadierno et al., "Bis(allyl)-Ruthenium(IV) Complexes as Highly Efficient Catalysts for the Redox Isomerization of Allylic Alcohols into Carbonyl Compounds in Organic and Aqueous Media: Scope, Limitations, and Theoretical Analysis of the mechanism", J. Am. Chem. Soc., 2006, 128 (4), 1360-1370.
Diaz-Alvarez et al., "Patented Routes for the Preparation of the Morphinan Derivatives Hydromorphone and Hydrocodone Via Catalytic Isomerization", Recent Patents on Catalysis, 2012, vol. 1, No. 1, 43-50.
"OECD Guideline for the Testing of Chemicals", 105, OECD, 1995.
Tohma et al., "Facile and Clean Oxidation of Alcohols in Water Using Hypervalent Iodine(III) Reagents", Angew. Chem. Int. Ed., 2000, 39(7), 1306-1308.
Zhang et al, "14-Hydroxylation of Opiates: Catalytic Direct Autoxidation of Codeinone to 14-Hydroxycodeinone", J. Am. Chem. Soc., 2005127 (20), 7286-7287.

* cited by examiner

*Primary Examiner* — Charanjit Aulakh
(74) *Attorney, Agent, or Firm* — Lerner, David, Littenberg, Krumholz & Mentlik, LLP

(57) ABSTRACT

There is provided a novel process for the preparation of a compound of formula I, wherein $R^1$, $R^2$ and $R^3$ are as described in the description, by conversion of a corresponding allylic alcohol.

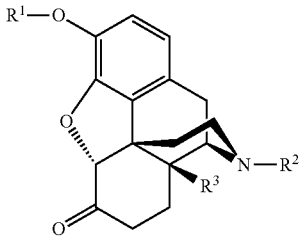

23 Claims, No Drawings

PREPARATION OF SATURATED KETONE MORPHINAN COMPOUNDS BY CATALYTIC ISOMERISATION

The present invention relates to a new redox isomerisation process step, for instance in the synthesis of certain semi synthetic opioids/alkaloids (including opioid receptor agonists, antagonists and other derivatives thereof) and/or intermediates thereto. In particular, the invention relates to new processes for modifying semi synthetic opioids/alkaloids that are structurally related to morphine.

Semi synthetic opioids include morphine, codeine, morphinone, codeinone, 14-hydroxymorphinone, 14-hydroxycodeinone, oxymorphone, oxycodone, hydromorphone and hydrocodone. These compounds can be prepared from starting materials such as morphine, codeine, oripavine and thebaine, or even from each other.

Traditionally, hydrocodone and hydromorphone have been synthesized in a two-step sequence from codeine and morphine: hydrogenation followed by an Oppenauer oxidation. The process is cumbersome and, for hydromorphone, low yielding. More recently hydrocodone and hydromorphone have been prepared from thebaine and oripavine respectively in a two step sequence which includes a selective hydrogenation followed by hydrolysis of the resulting enol ether.

The use of metal complexes for catalysing the redox isomerisation of allylic alcohols such as morphine and codeine is known. Processes in which a transition metal catalyst is used to isomerize the allylic alcohol to the desired ketone derivative are known. This methodology condenses two steps into one and avoids the use of stoichiometric reagents in the Oppenauer oxidation.

US 2011/0071016, US 2010/0261904 and US 2010/0261907 disclose reactions such as these using ruthenium-based catalysts to achieve this transformation in a one-pot procedure.

The use of rhodium-based catalysts in one-pot redox isomerisation reactions is disclosed in US 2010/0261906, U.S. Pat. No. 7,399,859, U.S. Pat. No. 5,847,142 and WO 98/05667.

However, residual metal catalyst often remains in the product and yields can be relatively low. It is desirable to reduce the amount of residual metal catalyst that remains as the catalyst is often expensive and may also be toxic and/or harmful to the environment, as may be the solvent.

The isolation may be simplified by the choice of the reaction medium, i.e. the product may be precipitated and isolated by filtration, with the catalyst remaining in the solvent system.

It is also desirable to reduce the amount of the α,β-unsaturated ketone derivative (e.g. codeinone, morphinone) that is present in the final product, due to potentially adverse toxicological properties that can be associated with such derivatives. International patent applications nos. WO 2012/003468 and WO 2008/070658 and U.S. Pat. Nos. 7,674,800 and 7,851,482 disclose processes for producing opiates in their ketone forms, such as oxycodone and oxymorphone, containing reduced amounts of the enone derivatives.

The present invention addresses some of the problems associated with the processes of the prior art.

The listing or discussion of an apparently prior-published document in this specification should not necessarily be taken as an acknowledgement that the document is part of the state of the art or common general knowledge.

According to a first aspect of the present invention, there is provided a process for the preparation of a compound of formula I,

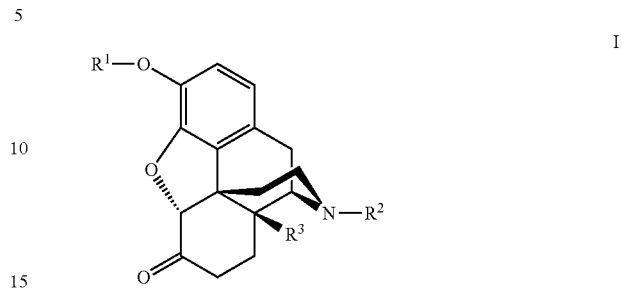

wherein:
$R^1$ represents hydrogen, $C_{1-18}$ alkyl, $C_{2-18}$ alkenyl, $C_{2-18}$ alkynyl or $C_{3-18}$ cycloalkyl, (which latter four groups are optionally substituted by one or more halo atoms) or a suitable hydroxy protecting group;

$R^2$ represents hydrogen or $C_{1-18}$ alkyl, $C_{2-18}$ alkenyl, $C_{2-18}$ alkynyl or $C_{3-18}$ cycloalkyl, (which latter four groups are optionally substituted by one or more halo atoms), or a suitable nitrogen protecting group; and $R^3$ represents hydrogen, —OH, $C_{1-18}$ alkyl, $C_{1-18}$ alkoxy, $C_{2-18}$ alkenyl, $C_{2-18}$ alkynyl, $C_{3-18}$ cycloalkyl, (which latter five groups are optionally substituted by one or more halo atoms) or —OR$^p$ wherein R$^p$ is a suitable hydroxy protecting group;

which process comprises contacting a compound of formula II,

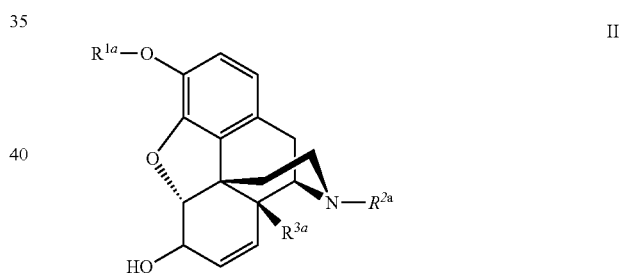

wherein $R^{1a}$, $R^{2a}$ and $R^{3a}$ are defined according to $R^1$, $R^2$ and $R^3$, respectively;
with:
(i) a rhodium complex; and
(ii) an organic additive selected from the group consisting of:
(a) alcohols of formula IIIa,

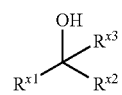

wherein $R^{x1}$, $R^{x2}$ and $R^{x3}$ independently represent hydrogen, a $C_{1-6}$ alkyl group, a $C_{2-6}$ alkenyl group, an aryl group or a heteroaryl group (which latter four groups may be optionally substituted by one or more halo atoms or $C_{1-4}$ alkyl groups); or any two of $R^{x1}$, $R^{x2}$ and $R^{x3}$ are linked together, along with the requisite carbon atom to which they are attached, to form a 4- to 8-membered cyclic alcohol, optionally containing one or more unsaturated bonds within the ring, and which ring is optionally substituted by one or more halo atoms or $C_{1-4}$ alkyl groups;

(b) ketones of formula IIIb,

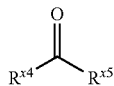

IIIb wherein $R^{x4}$ and $R^{x5}$ independently represent a $C_{1-4}$ alkyl group, a $C_{2-4}$ alkenyl group, an aryl group or a heteroaryl group (which four groups may be optionally substituted by one or more halo atoms or $C_{1-4}$ alkyl groups); or $R^{x4}$ and $R^{x5}$ are linked together, along with the requisite carbon atom to which they are attached, to form a 4- to 8-membered cyclic ketone, optionally containing one or more unsaturated bonds within the ring, and which ring is optionally substituted by one or more halo atoms or $C_{1-4}$ alkyl groups;

(c) ethers of formula IIIc,

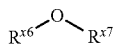

IIIc wherein $R^{x6}$ and $R^{x7}$ independently represent a $C_{1-4}$ alkyl group, or a $C_{2-4}$ alkenyl group (which groups may be optionally substituted by one or more halo atoms or $C_{1-4}$ alkyl groups); or $R^{x6}$ and $R^{x7}$ are linked together, along with the requisite oxygen atom to which they are attached, to form a 4- to 7-membered cyclic ether, optionally containing one or more unsaturated bonds within the ring, and which ring is optionally substituted by one or more halo atoms or $C_{1-4}$ alkyl groups; and (d) thioethers of formula IIId,

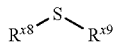

IIId wherein $R^{x8}$ and $R^{x9}$ independently represent a $C_{1-4}$ alkyl group, or a $C_{2-4}$ alkenyl group (which groups may be optionally substituted by one or more halo atoms or $C_{1-4}$ alkyl groups); or $R^{x8}$ and $R^{x9}$ are linked together, along with the requisite sulfur atom to which they are attached, to form a 4- to 7-membered cyclic thioether, optionally containing one or more unsaturated bonds within the ring, and which ring is optionally substituted by one or more halo atoms or $C_{1-4}$ alkyl groups;

which process is hereinafter referred to as "the process of the invention".

In particular embodiments of the invention, the organic additive used in the process of the invention is a compound selected from the group consisting of alcohols of formula IIIa, ketones of formula IIIb and ethers of formula IIIc.

The process of the invention may be performed employing salts, solvates or protected derivatives (of compounds of formula II), thereby producing compounds that may or may not be produced in the form of a (e.g. corresponding) salt or solvate, or a protected derivative thereof (of compounds of formula I). Particular salts that may be mentioned include organic acid salts such as tartrate salts (e.g. bitartrate salts) and inorganic acid salts such as hydrohalide salts (e.g. hydrochloride salts). However, in certain embodiments of the invention, the process of the invention is not performed on a protected derivative but is rather performed using the salt or solvate or, in particular, using the free base of the compound of formula II in order to obtain the free base of the final product.

Protecting groups may be removed in accordance with techniques which are well known to those skilled in the art and as described hereinafter.

It is specifically stated herein that compounds of formulae I and II may be protected. For instance, the hydroxy moiety may be protected, i.e. $R^1$ and/or $R^{1a}$ may represent a suitable hydroxy protecting group. Alternatively, or additionally, $R^3$ and/or $R^{3a}$ may represent a hydroxy moiety protected by a suitable hydroxy protecting group. Suitable protecting groups for hydroxy include trialkylsilyl and diarylalkyl-silyl groups (e.g. tert-butyldimethylsilyl, tert-butyldiphenylsilyl or trimethylsilyl), tetrahydropyranyl, alkylaryl groups (e.g. optionally substituted benzyl), alkylcarbonyl groups (e.g. methyl- and ethylcarbonyl groups), aroyl groups (e.g. optionally substituted benzoyl) and sulfonyl groups (to form e.g. aromatic sulfonyl (e.g. tosyl) esters, so forming e.g. a —O—S(O)$_2$-[aryl/heteroaryl] protecting group such as —O—S(O)$_2$-[4-methylphenyl]). In certain embodiments of the invention, the protecting groups are optionally substituted benzoyl groups, alkylcarbonyl (e.g. acetyl), benzyl and toluenesulfonyl groups. In particular embodiments of the invention, the protecting groups are optionally substituted benzoyl, in particular benzoyl.

Examples of nitrogen protecting groups which may be used, for example protecting groups at the position denoted as $R^2$ and/or $R^{2a}$, include carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-toluensulfonyl (Tosyl, Ts), p-bromobenzenesulfonyl (Brosyl, Bs), methanesulfonyl (Mesyl, Ms), 2- or 4-nitrobenzenesulfonyl (Nosyl, Ns), trifluoromethanesulfonyl (triflyl, Tf), 5-(dimethylamino)naphthalene-1-sulfonyl (Dansyl, Ds), and 2-napthalenesulfonyl (Nps). Other groups that $R^2$ may represent include methyl, ethyl, propyl, propenyl and butyl (e.g. cyclopropylmethyl).

The use of protecting groups is described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

Compounds employed in or produced by the processes described herein (i.e. those involving the process of the invention) may exhibit tautomerism. The process of the invention therefore encompasses the use or production of such compounds in any of their tautomeric forms, or in mixtures of any such forms.

The compounds of formulae I and II are of defined stereochemistry. However, the process of the invention may include reactions with all isomers of formula II to form all isomers of formula I. For instance, compounds employed in or produced by the processes described herein (i.e. those involving the process of the invention) may also contain one or more asymmetric carbon atoms and may therefore exist as enantiomers or diastereoisomers, and may exhibit optical activity. The process of the invention thus encompasses the use or production of such compounds in any of their optical or diastereoisomeric forms, or in mixtures of any such forms.

Unless otherwise specified, alkyl groups as defined herein may be straight-chain or, when there is a sufficient number (i.e. a minimum of three) of carbon atoms be branched-chain. Cycloalkyl groups may be fully or partly cyclic.

Further, the compounds employed in or produced by the processes described herein may contain double bonds and may thus exist as E (entgegen) and Z (zusammen) geometric isomers about each individual double bond. All such isomers and mixtures thereof are included within the scope of the invention.

The term "aryl", when used herein, includes $C_{6-10}$ groups. Such groups may be monocyclic, bicyclic or tricyclic and, when polycyclic, be either wholly or partly aromatic. $C_{6-10}$ aryl groups that may be mentioned include phenyl, naphthyl, indenyl, and the like. For the avoidance of doubt, the point of attachment of substituents on aryl groups may be via any carbon atom of the ring system.

Unless otherwise specified, the term "heteroaryl" when used herein refers to an aromatic group containing one or more heteroatom(s) (e.g. one to four heteroatoms) preferably selected from N, O and S. Heteroaryl groups include those which have from 5 to 10 members (e.g. from 5 to 7) and may be monocyclic or bicyclic, provided that at least one of the rings is aromatic (so forming, for example, a mono- or bicyclic heteroaromatic group). When the heteroaryl group is polycyclic the point of attachment may be via any atom including an atom of a non-aromatic ring. However, when heteroaryl groups are polycyclic (i.e. bicyclic), they are preferably linked to the rest of the molecule via an aromatic ring. Heteroaryl groups that may be mentioned include benzofuranyl, furanyl, imidazolyl, indolyl, isoquinolinyl, oxazolyl, pyrazinyl, pyrazolyl, pyridazinyl, pyridyl, pyrimidinyl, pyrrolyl, quinolinyl, tetrahydroquinolinyl, thiazolyl and thienyl. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom). Heteroaryl groups may also be in the N- or S-oxidised form.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is from 3 to 10 (e.g. from 5 to 8). Further, such heterocycloalkyl groups may be saturated or unsaturated containing one or more double and/or triple bonds, forming for example a heterocycloalkenyl (where q is the upper limit of the range) group. Heterocycloalkyl groups that may be mentioned include azetidinyldioxolanyl, dioxanyl, imidazolidinyl, morpholinyl, piperazinyl, piperidinyl, non-aromatic pyranyl, pyrazolidinyl, pyrrolidinyl, and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom). Heterocycloalkyl groups may also be in the N- or S-oxidised form.

For the avoidance of doubt, the term "bicyclic" (e.g. when employed in the context of heterocycloalkyl groups) refers to groups in which the second ring of a two-ring system is formed between two adjacent atoms of the first ring.

The terms "halo", "halogen" and "halide", when used herein, include fluoro, chloro, bromo and iodo.

It is stated herein that the process of the invention is performed in the presence of a rhodium complex. In particular embodiments, the rhodium complex is a rhodium (III) complex or, preferably, a rhodium (I) complex.

In an embodiment of the invention, the rhodium complex is dissolved in an aqueous phase and the metal can not only be readily recovered, but also it does not affect the quality of the product. Additionally, the process will further benefit economically by the use of water as solvent, or an aqueous solvent system, as it is inexpensive and environmentally benign.

The process of the invention may be performed in the presence of any suitable solvent system, particularly a protic solvent system, for instance any aqueous solvent system that allows the dissolution of the rhodium complex. The term "aqueous solvent system" is intended to include solvent systems that comprise water (e.g. comprising at least 20% water) and optional additional non-aqueous solvents. Protic solvent systems that may be mentioned in this respect include alcohols (e.g. methanol, ethanol, isopropanol, tert-butanol or ethylene glycol), water, and mixtures of either an alcohol or water with one or more polar organic solvents such as acetonitrile, alcohols (e.g. methanol, ethanol, isopropanol, tert-butanol or ethylene glycol), dimethyl formamide (DMF), dimethyl sulfoxide (DMSO), tetrahydrofuran (THF), dimethyl ether or ketone-based solvents (e.g. acetone, butanone, methyl ethyl ketone (MEK), diethyl ketone (DEK) or methyl isobutyl ketone). Particular solvent systems that may be mentioned in this respect include mixtures comprising water and an alcohol (e.g. a mixture of water and either isopropanol or tert-butanol). The solvent system employed in the process of the invention may be a mixture of water and a plurality of the aforementioned non-aqueous solvents. However, in particular embodiments of the invention, it consists predominantly of water or, more particularly, it consists almost exclusively (or essentially) of water. Particular aqueous solvent systems that may be mentioned include those that consist of from 30% to 60% (e.g. from 40% to 50%) water by weight or by volume. Other aqueous solvent systems that may be mentioned in this respect include those that consist of at least 30%, at least 40% at least 50%, at least 60%, at least 70%, at least 80% or at least 90% water by weight or by volume, such as at least 95, 96, 97, 98 or 99% water (e.g. about 100%) by weight or by volume.

The solvent for the reaction may be degassed prior to introduction of any of the starting materials. Degassing may be achieved through a vacuum/inert gas (e.g. nitrogen) purge cycle, or any other method known to the skilled person. Degassing may be performed to reduce the level of dissolved oxygen in the solvent. The amount of dissolved oxygen in the solvent prior to the introduction of the starting materials may be reduced so as to maintain as high an efficiency for the reaction as possible. In particular embodiments of the process of the invention, the amount of dissolved oxygen in the solvent prior to the introduction of the starting materials is below about 10 ppm (e.g. below about 1 ppm, such as below about 0.5 ppm).

The amount of the rhodium complex should be sufficient for the process of the invention to proceed to completion. For instance, at least 0.05 mol % of the rhodium complex is employed, relative to the compound of formula II. In particular embodiments of the invention, at least about 0.1 mol % and up to about 10 mol % is employed, such as from about 0.5 to about 5 (e.g. about 1) mol % of the rhodium complex.

The process of the invention may be performed at room temperature or at elevated temperature. In particular embodiments of the invention, the process of the invention is performed at elevated temperature as this has the advantage of the redox isomerisation process proceeding to higher levels of conversion compared to lower temperatures (where high conversion is difficult). For example, the process of the invention may be performed at temperatures greater than about 60° C., for instance greater than about 70° C. (e.g. from about 65° C. to about 140° C., such as from about 75° C. to about 120° C., or from about 80° C. to about 110° C.). The upper temperature limit for the process of the invention is generally dependent upon the boiling point of the solvent system that is employed. Reactions may be conducted at higher temperatures, for example through the use of high pressure systems, such as an autoclave or a sealed reactor which is capable of containing the reaction mixture at above ambient air pressure. In particular embodiments of the invention, the temperature range is from about 70° C. to about 110° C. and, particularly, from about 95° C. to about 105° C. (e.g. about 100° C.). Such temperature ranges are particularly suited to the certain (e.g. aqueous) solvent systems that may be employed in the process of the invention.

In certain embodiments of the invention, the mixture including the compound of formula II and solvent (in particular, predominantly water) is heated to about the particular temperatures at which the process of the invention should take place. Thereafter, the pre-formed rhodium complex may be added such that the temperature of the process is maintained within the particular ranges specified hereinbefore. Alternatively, the mixture including the compound of formula II and solvent (in particular, predominantly water) is heated to about the particular temperatures at which the process of the invention should take place, following which the components needed to form the rhodium complex (e.g. a precursor complex together with one or more ligands) may be added simultaneously or sequentially to the mixture containing the compound of formula II at a rate such that the temperature of the process is maintained within the particular ranges specified hereinbefore.

In certain embodiments of the invention, the process comprises an initial step of reacting a compound of either formula IV or V, as defined below, with a compound of formula VI, as defined below. This initial step may be performed in the presence of the compound of formula II. However, in particular embodiments of the invention, this initial step is performed prior to bringing the compound of formula II into contact with the resulting rhodium complex. In such embodiments, the initial step of reacting a compound of either formula IV or V, with a compound of formula VI, is performed in an aqueous solvent system, i.e. a solvent system that comprises predominantly water (e.g. at least 50% water), optionally further containing one or more polar organic solvents such as acetonitrile, alcohols, dimethyl formamide (DMF), dimethyl sulfoxide (DMSO), or ketone-based solvents.

In particular embodiments of the invention, the rhodium complex is added to the compound of formula II (e.g. when the latter compound is already in a mixture with solvent, which may be employed in the process of the invention). In particular, the rhodium complex is added over a certain period of time so as to maintain the temperature of the process of the invention at the particular ranges (mentioned hereinbefore). For instance, the rhodium complex may be added over a period of up to 30 minutes, e.g. up to 15 minutes, and, in particular, up to about 10 minutes.

In other embodiments of the invention, the rhodium complex may be formed in situ (i.e. in the presence of the compound of formula II. Such a process may involve the addition of a compound of either formula IV or V, as defined below, and a compound of formula VI, as defined below, to a mixture containing a compound of formula II and solvent (in particular, predominantly water). In particular embodiments of processes, one or more of the compounds of formulae IV, V and VI may be added over a certain period of time so as to maintain the temperature of the process of the invention at the particular ranges (mentioned hereinbefore). For instance, one or more of the compounds of formulae IV, V and VI may be added over a period of up to about 30 minutes, e.g. up to about 15 minutes, and, in particular, up to about 10 minutes.

In certain embodiments of the invention, both the starting material (the compound of formula II) and the product (compound of formula I) are only partially soluble, or essentially insoluble, in the solvent system used for the process. Embodiments of the invention therefore include those in which the compound of formula I is obtained from the reaction mixture by filtration, or any other solid/liquid separation method known to the skilled person.

In a further embodiment of the invention, the compound of formula I that may be separated from the solvent may be further purified by crystallisation from a suitable solvent. For instance, the compound of formula I may be dissolved to obtain a solution of that compound in a solvent (in particular, water or an organic solvent, e.g. an alcohol, a ketone, or an aromatic solvent such as toluene, or a mixture of water and an organic solvent, e.g. a mixture of water and an alcohol). The compound of formula I (in solvent, e.g. toluene or a mixture of water and tert-butyl alcohol) may be diluted with a different solvent in order to promote the crystallisation (in particular embodiments, that different solvent is an ether, such as methyl tert-butyl ether, or an alcohol, such as tert-butyl alcohol). In an alternative embodiment, the compound of formula I may be crystallised from the solution containing the compound by increasing the concentration of the compound of formula I in the solution and/or by cooling the solution. The increased concentration may be achieved by any appropriate means, which would be known to the person skilled in the art, for example by removing a portion of the solvent (e.g. by distillation).

In certain embodiments of the invention, the rhodium complex is a water-soluble rhodium complex. The term "water-soluble rhodium complex" when used herein refer to a rhodium-containing complex which has a solubility in water of at least 0.01 g per 100 g (i.e. at least 0.1 g/L) water at 20° C. In particular embodiments of the invention, the water-soluble rhodium complex has a solubility in water of at least 0.1 g (e.g. at least 1 g) per 100 g (i.e. at least 1 g/L (e.g. at least 10 g/L)) water at 20° C.

Solubility in water may be determined by any method known to the skilled person, for example, the OECD Guideline for the Testing of Chemicals no. 105, OECD, 1995.

Particular rhodium complexes that may be used in the present invention are those that contain at least one water-soluble phosphine as a ligand. Such a rhodium complex can be prepared from a water-soluble phosphine and a precursor rhodium complex (which precursor rhodium complex may or may not be relatively water-soluble).

Alternatively, the rhodium complex that may be used in the present invention is one that contains a phosphine having relatively low water solubility. By "relatively low water solubility" it is meant that the solubility of the substance in water at 20° C. is less than about 0.01 g (e.g. less than about $10^{-3}$ g) per 100 g water (for example, less than about $10^{-5}$ g per 100 g water).

In certain embodiments of the invention, where the rhodium complex is prepared from a water-soluble phosphine and a precursor rhodium complex, the rhodium complex is pre-formed prior to addition to the compound of formula II. By pre-formed, it is meant that the water-soluble phosphine and the precursor rhodium complex are mixed together in a suitable solvent, for example, the same solvent that is to be used for the redox isomerisation reaction, and stirred together for a sufficient duration (e.g. 15 minutes) before the resulting solution of the rhodium complex is brought into contact with either the compound of formula II or the organic additive.

In other embodiments of the invention, the rhodium complex is formed in situ, e.g. from a water-soluble phosphine and a precursor rhodium complex. For example, the water-soluble phosphine and the precursor rhodium complex may be mixed together in the presence of the compound of formula II. In a particular embodiment, the water-soluble phosphine, the precursor rhodium complex and the compound of formula II are mixed together before the organic additive is added.

In embodiments of the invention, where the rhodium complex is prepared from a phosphine having a relatively low water solubility and a precursor rhodium complex, the rhodium complex may similarly be pre-formed prior to addition to the compound of formula II.

When the phosphine contains two, or particularly, one phosphorus atom capable of coordinating to rhodium, formation of the rhodium complex may be achieved by mixing the water-soluble phosphine and the precursor rhodium complex in a molar ratio (of phospine:rhodium precursor) of at least 1:1 (e.g. at least 1.5:1), in particular from 1:1 to 3:1 (such as about 2:1). The formation of the rhodium complex may be conducted in a suitable solvent, for instance any solvent that allows the dissolution of the rhodium complex. Solvents that may be mentioned in this respect include water, and mixtures of water with one or more polar organic solvents such as alcohols (e.g. methanol, ethanol, isopropanol or tert-butanol), dimethyl formamide (DMF), dimethyl sulfoxide (DMSO), or ketone-based solvents (e.g. acetone, butanone or methyl isobutyl ketone). The solvent system employed in this aspect of the process of the invention may be a mixture of water and a plurality of the aforementioned non-aqueous solvents. However, in particular embodiments, it consists predominantly of water, e.g. it consists almost exclusively of water.

In particular embodiments of the invention, the rhodium complex is a rhodium complex that is prepared from a water-soluble phosphine and either a precursor rhodium complex of formula IV,

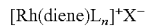    IV or a dimeric precursor rhodium complex of formula V,

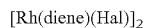    V wherein diene represents a diene ligand such as COD (1,5-cyclooctadiene), bicyclo[2,2,1]heptadiene or norbornadiene, X represents a suitable anion (such as a halide or, particularly, a non-coordinating anion, such as BARF (i.e. a tetrakis(polyfluoroaryl)borate), $SbF_6^-$, $BF_4^-$, $ClO_4^-$, $PF_6^-$, $HSO_4^-$, $H_2PO_4^-$, $CH_3CO_2^-$, $CF_3CO_2^-$, $CF_3SO_3^-$ or $PhCO_2^-$), L represents a neutral ligand (for example a weakly coordinating ligand such as acetonitrile, acetone, DMF, THF, DMSO or benzonitrile), n represents from 1 to 3 (e.g. 2), and Hal represents a halide (such as chloride) or a hydroxide.

When the rhodium complex is prepared from a water-soluble phosphine and a dimeric precursor rhodium complex of formula V, the rhodium complex is formed in the presence of a salt of formula AY, wherein: A represents an organic cation, such as triphenyl carbenium, or an inorganic cation, such as $Ag^+$, $Na^+$, $K^+$ or $Li^+$; and Y represents a non-coordinating anion such as BARF, $SbF_6^-$, $BF_4^-$, $PF_6^-$, $HSO_4^-$, $H_2PO_4^-$, $CH_3CO_2^-$, $CF_3CO_2^-$, $CF_3SO_3^-$ or $PhCO_2^-$.

In particular embodiments of the invention, the rhodium complex is prepared from a water-soluble phosphine and a precursor rhodium complex of formula IVA;

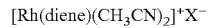    IVA wherein diene represents a diene ligand such as COD (1,5-cyclooctadiene), bicyclo[2,2,1]heptadiene or norbornadiene, and X represents a suitable anion (such as a halide or, particularly, a non-coordinating anion, such as BARF, $SbF_6^-$, $BF_4^-$, $ClO_4^-$, $PF_6^-$, $HSO_4^-$, $H_2PO_4^-$, $CH_3CO_2^-$, $CF_3CO_2^-$, $CF_3SO_3^-$ or $PhCO_2^-$.

By using this complex, the relative amount of catalyst required can be reduced (i.e. catalyst loading can be kept to a minimum), since the in-situ formed catalyst is extremely efficient in transforming the allylic alcohol to the ketone. Thus in the claimed process the raw material cost will be predominantly the cost of starting materials, for example, the allylic alcohols morphine and codeine.

In embodiments of the invention, the rhodium complex is a water soluble complex prepared from a phosphine and a cationic rhodium complex.

In particular embodiments of the invention, the rhodium complex is prepared from a water-soluble phosphine and $[Rh(COD)(CH_3CN)_2](BF_4)$.

Water-soluble phosphines which may be used in the present invention include phosphines having a water-solubility of at least 0.1 g per 100 g water at 20° C. (i.e. 1 g/L). In particular embodiments, the water-soluble phosphine has a solubility in water of at least 0.5 g (e.g. at least 5 g) per 100 g (i.e. at least 5 g/L (e.g. at least 50 g/L)) water at 20° C.

In particular, water-soluble phosphines which may be used in the present invention include those in which each phosphorus atom of the phosphine is bound to three substituents via a carbon atom, wherein at least one of those three substituents bears at least one hydrophilic moiety. Hydrophilic moieties that may be mentioned in this respect include $-OR^v$, $-N(R^w)R^x$, $-C(O)-R^y$, $-S(O)_2OR^z$, and salts thereof, wherein each $R^v$ to $R^z$ independently represents hydrogen, or a $C_{1-4}$ alkyl, and wherein $R^w$ and $R^x$ groups attached to substituents on the same phosphorus atom may together form a $C_{1-3}$ alkylene chain.

Such phosphines include compounds of formula VI,

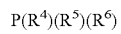    VI wherein each of $R^4$, $R^5$ and $R^6$ independently represents a $C_{1-6}$ alkyl or an aryl group, both of which groups may be optionally substituted by one or more groups selected from the list consisting of $-OR^{6a}$, $-SO_2OH$, $C(O)R^{7a}$, $-N(R^{8a})R^{9a}$, or a salt of $-SO_2OH$ or $-N(R^{8a})R^{9a}$; or any two of $R^4$, $R^5$ and $R^6$ may be linked together to form a 4- to 7- (e.g. 5- to 6-) membered ring, optionally containing one or more heteroatoms (for example, in addition to the phosphorus atom that is already present, one or more heteroatoms selected from oxygen, nitrogen and sulfur) and which ring is optionally substituted by one or more substituents selected from —OR$^{6b}$, —SO$_2$OH, C(O)R$^{7b}$, —N(R$^{8b}$)R$^{9b}$, or a salt of —SO$_2$OH or —N(R$^{8b}$)R$^{9b}$;

or all three of R$^4$, R$^5$ and R$^6$ may be linked together to form a cage-like structure (e.g. having an adamantane-type skeleton) optionally containing one or more heteroatoms (for example, in addition to the phosphorus atom that is already present, one or more heteroatoms selected from oxygen, nitrogen and sulfur), and which cage-like structure is optionally substituted by one or more substituents selected from —OR', —SO$_2$OH, C(O)R$^{7c}$, —N(R$^{8c}$)R$^{9c}$, or a salt of —SO$_2$OH or —N(R$^{8c}$)R$^{9c}$;

wherein R$^{6a}$ R$^{6b}$, R$^{6c}$, R$^{7a}$, R$^{7b}$, R$^{7c}$, R$^{8a}$, R$^{8b}$, R$^{8c}$, R$^{9a}$ R$^{9b}$, and R$^{9c}$ are each independently selected from hydrogen, and C$_{1-4}$ alkyl.

Particular salts of —SO$_2$OH that may be mentioned include alkali metal and alkaline earth metal salts. Examples of such alkali metal and alkaline earth metal salts include cesium and lithium salts and, particularly, sodium and potassium salts.

Particular acid addition salts of —N(R$^{8a}$)R$^{9a}$, —N(R$^{8b}$)R$^{9b}$ and —N(R$^{8c}$)R$^{9c}$ that may be mentioned include salts of HCl, H$_2$SO$_4$, H$_3$PO$_4$ and organic acids (e.g. acetic acid, methanesulfonic acid or toluenesulfonic acid derivatives (such as p-toluenesulfonic acid)).

Particular phosphines that may be mentioned include:

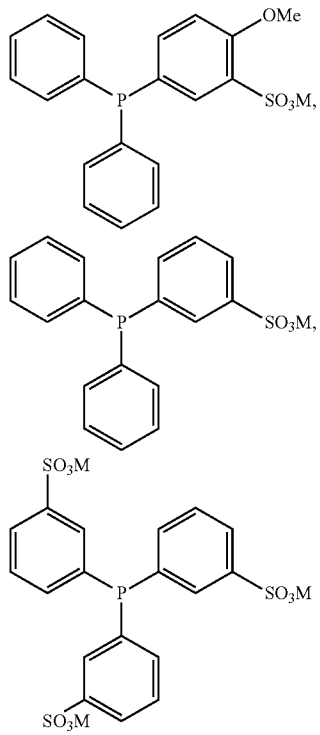

and 1,3,5-triaza-7-phosphaadamantane (PTA), which latter phosphine is optionally alkylated with one or more (e.g. one) methyl groups (thus including 1-methyl-1,3,5-triaza-7-phosphaadamantane); wherein M represents an alkali metal selected from lithium, cesium and, particularly, potassium and sodium.

A particular phosphine that may be mentioned for use in the processes of the present invention is 1,3,5-triaza-7-phosphaadamantane (PTA),

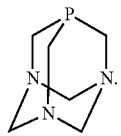

Derivatives of 1,3,5-triaza-7-phosphaadamantane may also be used, for example, derivatives in which one or more (e.g. one) of the nitrogen atoms is alkylated (e.g. methylated) by a C$_{1-4}$ alkyl group.

Particular phosphines having relatively low water solubility that may be mentioned include triaryl phosphines (e.g. triphenyl phosphine) and trialkyl phosphines (e.g. triethylphosphine or trimethylphosphine).

A particular rhodium complex that may be mentioned in this respect is that formed by reacting [Rh(COD)(CH$_3$CN)$_2$](BF$_4$) with 1,3,5-triaza-7-phosphaadamantane or a derivative thereof.

The organic additive is a compound selected from the group consisting of:

(a) alcohols of formula IIIa,

wherein R$^{x1}$, R$^{x2}$ and R$^{x3}$ independently represent hydrogen, a C$_1$-6 alkyl group, a C$_{2-6}$ alkenyl group, an aryl (e.g. a C$_{6-10}$ aryl) group or a heteroaryl (e.g. a 5- to 10-membered heteroaryl) group (which latter four groups may be optionally substituted by one or more halo atoms or C$_{1-4}$ alkyl groups); or any two of R$^{x1}$, R$^{x2}$ and R$^{x3}$ are linked together, along with the requisite carbon atom to which they are attached, to form a 4- to 8-membered cyclic alcohol, optionally containing one or more unsaturated bonds within the ring, and which ring is optionally substituted by one or more halo atoms or C$_{1-4}$ alkyl groups;

(b) ketones of formula IIIb,

wherein R$^{x4}$ and R$^{x5}$ independently represent a C$_{1-4}$ alkyl group, a C$_{2-4}$ alkenyl group, an aryl (e.g. a C$_{6-10}$ aryl) group or a heteroaryl (e.g. a 5- to 10-membered heteroaryl) group (which four groups may be optionally substituted by one or more halo atoms or C$_{1-4}$ alkyl groups); or R$^{x4}$ and R$^{x5}$ are linked together, along with the requisite carbon atom to which they are attached, to form a 4- to 8-membered cyclic ketone, optionally containing one or more unsaturated bonds within the ring, and which ring is optionally substituted by one or more halo atoms or C$_{1-4}$ alkyl groups;

(c) ethers of formula IIIc,

wherein R$^{x6}$ and R$^{x7}$ independently represent a C$_{1-4}$ alkyl group, or a C$_{2-4}$ alkenyl group (which groups may be optionally substituted by one or more halo atoms or C$_{1-4}$ alkyl groups); or $R^{x6}$ and $R^{x7}$ are linked together, along with the requisite oxygen atom to which they are attached, to form a 4- to 7-membered (e.g. a 5-membered) cyclic ether, optionally containing one or more unsaturated bonds within the ring, and which ring is optionally substituted by one or more halo atoms or $C_{1-4}$ alkyl groups; and (d) thioethers of formula IIId,

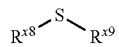

IIId wherein $R^{x8}$ and $R^{x9}$ independently represent a $C_{1-4}$ alkyl group, or a $C_{2-4}$ alkenyl group (which groups may be optionally substituted by one or more halo atoms or $C_{1-4}$ alkyl groups); or $R^{x8}$ and $R^{x9}$ are linked together, along with the requisite sulfur atom to which they are attached, to form a 4- to 7-membered (e.g. a 5-membered) cyclic thioether, optionally containing one or more unsaturated bonds within the ring, and which ring is optionally substituted by one or more halo atoms or $C_{1-4}$ alkyl groups.

In particular embodiments of the invention, the organic additive used in the process of the invention is a compound selected from the group consisting of alcohols of formula IIIa, ketones of formula IIIb and ethers of formula IIIc.

In particular embodiments of the invention, the organic additive used in the present invention is:
(a) a compound of formula IIIa, as defined above, wherein $R^{x1}$, $R^{x2}$ and $R^{x3}$ each independently represents hydrogen or a $C_{1-4}$ alkyl group (such as methanol, ethanol, propanol (e.g. isopropanol) or butanol (e.g. n-butanol, sec-butanol isobutanol, or, particularly, tert-butanol);
(b) a compound of formula IIIb, as defined above, wherein $R^{x4}$ and $R^{x5}$ each independently represents a $C_{1-4}$ alkyl group (such as acetone, butanone or methyl iso-butyl ketone); (c) a compound of formula IIIc, as defined above, wherein $R^{x6}$ and $R^{x7}$ each independently represents a $C_{1-2}$ alkyl group (such as dimethyl ether or diethyl ether), or wherein $R^{x6}$ and $R^{x7}$ are linked together, along with the requisite oxygen atom to which they are attached, to form a 5- to 6-membered cyclic ether (which ring may be optionally substituted by one or more halo atoms or methyl groups) (such as tetrahydrofuran or methyl-tetrahydrofuran); or
(d) a compound of formula IIId, as defined above, wherein $R^{x8}$ and $R^{x9}$ each independently represents a $C_{2-4}$ alkyl group (such as dibutylsulfide), or wherein $R^{x8}$ and $R^{x9}$ are linked together, along with the requisite sulfur atom to which they are attached, to form a 5- to 6-membered cyclic thioether (which ring may be optionally substituted by one or more halo atoms or methyl groups) (such as thiophene or tetrahydrothiophene).

In other particular embodiments of the invention, the organic additive used in the present invention is:
(a) a compound of formula IIIa, as defined above, wherein $R^{x1}$, $R^{x2}$ and $R^{x3}$ each independently represents hydrogen or a $C_{1-4}$ alkyl group (such as methanol, ethanol, propanol (e.g. isopropanol) or butanol (e.g. n-butanol, sec-butanol isobutanol, or, particularly, tert-butanol);
(b) a compound of formula IIIb, as defined above, wherein $R^{x4}$ and $R^{x5}$ each independently represents a $C_{1-4}$ alkyl group (such as acetone, butanone or methyl iso-butyl ketone); or (c) a compound of formula IIIc, as defined above, wherein $R^{x6}$ and $R^{x7}$ each independently represents a $C_{1-2}$ alkyl group (such as dimethyl ether or diethyl ether), or wherein $R^{x6}$ and $R^{x7}$ are linked together, along with the requisite oxygen atom to which they are attached, to form a 5- to 6-membered cyclic ether (which ring may be optionally substituted by one or more halo atoms or methyl groups) (such as tetrahydrofuran or methyl-tetrahydrofuran).

In other particular embodiments of the invention, the organic additive used in the present invention is:
(a) a compound of formula IIIa, as defined above, wherein $R^{x1}$, $R^{x2}$ and $R^{x3}$ each independently represents hydrogen, a $C_{1-4}$ alkyl group, a $C_{6-10}$ aryl group or a 5- to 10-membered heteroaryl group (which latter three groups may be optionally substituted by one or more halo atoms or $C_{1-4}$ alkyl groups);
(b) a compound of formula IIIb, as defined above, wherein $R^{x4}$ and $R^{x5}$ each independently represents a $C_{1-4}$ alkyl group, a $C_{6-10}$ aryl group or a 5- to 10-membered heteroaryl group (which three groups may be optionally substituted by one or more halo atoms or $C_{1-4}$ alkyl groups);
(c) a compound of formula IIIc, as defined above, wherein $R^{x6}$ and $R^{x7}$ are linked together, along with the requisite oxygen atom to which they are attached, to form a 5- to 6-membered cyclic ether (which ring may be optionally substituted by one or more halo atoms or methyl groups); or
(d) a compound of formula IIId, as defined above, wherein $R^{x8}$ and $R^{x9}$ independently represent a $C_{1-4}$ alkyl group, or a $C_{2-4}$ alkenyl group (which groups may be optionally substituted by one or more halo atoms or $C_{1-4}$ alkyl groups).

In other particular embodiments of the invention, the organic additive used in the present invention is:
(a) a compound of formula IIIa, as defined above, wherein $R^{x1}$, $R^{x2}$ and $R^{x3}$ each independently represents hydrogen, a $C_{1-4}$ alkyl group, a $C_{6-10}$ aryl group or a 5- to 10-membered heteroaryl group (which latter three groups may be optionally substituted by one or more halo atoms or $C_{1-4}$ alkyl groups);
(b) a compound of formula IIIb, as defined above, wherein $R^{x4}$ and $R^{x5}$ each independently represents a $C_{1-4}$ alkyl group, a $C_{6-10}$ aryl group or a 5- to 10-membered heteroaryl group (which three groups may be optionally substituted by one or more halo atoms or $C_{1-4}$ alkyl groups); or
(c) a compound of formula IIIc, as defined above, wherein $R^{x6}$ and $R^{x7}$ are linked together, along with the requisite oxygen atom to which they are attached, to form a 5- to 6-membered cyclic ether (which ring may be optionally substituted by one or more halo atoms or methyl groups).

Particular organic additives that may be mentioned include alcohols of formula IIIa and ketones of formula IIIb, as defined above.

In certain embodiments of the invention, the organic additive is not methanol. For example, particular organic additives that may be mentioned include those in which, when the organic additive is a compound of formula IIIa, at least one of $R^{x1}$, $R^{x2}$ and $R^{x3}$ is other than hydrogen, e.g. at least one of $R^{x1}$, $R^{x2}$ and $R^{x3}$ represents a $C_{1-4}$ alkyl group.

Particular organic additives that may be mentioned include acetone, isopropanol and, most particularly, tert-butanol.

The amount of the organic additive should be sufficient to reduce the amount of enone by-product in the product of the reaction compared to the product produced in the absence of an organic additive. In particular embodiments, the amount of organic additive that is present in the reaction is at least 0.5 equivalents, such as from 1 to 20 equivalents (e.g. from 2 to 10 equivalents), relative to the compound of formula II. In the most particular embodiments, amount of organic additive that is present in the reaction is from 7 to 9 equivalents, e.g. about 8 equivalents, relative to the compound of formula II. In particular embodiments, the organic additive is tert-butanol which is present in the reaction in an amount of from 7 to 9 equivalents, e.g. about 8 equivalents, relative to the compound of formula II.

The organic additive may be added to the reaction at any time. In particular embodiments, the compound of formula II is brought into contact with the organic additive before the compound of formula II is brought into contact with the rhodium complex.

In one embodiment:

(i) the compound of formula II is provided in a suitable solvent system, as defined above;

(ii) the rhodium complex is provided in an aqueous solvent system (e.g. a solvent system that consists predominantly of water);

(iii) the organic additive is added to the compound of formula II; and then (iv) the solution comprising the rhodium complex is added to the mixture comprising the compound of formula II and the organic additive.

In a particular embodiment:

(i) the compound of formula II is provided in a protic solvent system;

(ii) the rhodium complex is provided in an aqueous solvent system;

(iii) the organic additive is added to the compound of formula II; and then (iv) the solution comprising the rhodium complex is added to the mixture comprising the compound of formula II and the organic additive.

In another embodiment, the organic additive is mixed together with the compound of formula II (and any associated solvents), and then to this mixture is added a water-soluble phosphine and a precursor rhodium complex. For example:

(i) the compound of formula II is provided in a suitable solvent system, as defined above;

(ii) the organic additive is added to the mixture of a compound of formula II and a solvent system; and then (iii) a water-soluble phosphine and a precursor rhodium complex are added (either sequentially or simultaneously) to the mixture comprising the compound of formula II, the organic additive and the solvent system.

In other particular embodiments, the organic additive is mixed together with the compound of formula II (and any associated solvents), and the mixture is then stirred for a sufficient duration (e.g. 15 minutes) before the rhodium complex is brought into contact with the mixture containing the compound of formula II and the organic additive.

In particular embodiments, the addition of the organic additive to the compound of formula II is completed before the rhodium complex is added to the mixture comprising the compound of formula II and the organic additive. For embodiments in which the rhodium complex is formed in situ (i.e. in the presence of the compound of formula II), the addition of the organic additive to the compound of formula II may be completed before the water-soluble phosphine and the precursor rhodium complex are added to the mixture comprising the compound of formula II.

In particular embodiments of the invention, $R^1$ in the compound of formula I represents hydrogen, $C_{1-6}$ alkyl, $C_{2-6}$ alkenyl, $C_{2-6}$ alkynyl or $C_{3-6}$ cycloalkyl, (which latter four groups are optionally substituted by one or more halo atoms) or a suitable hydroxy protecting group. In particular embodiments of the invention, $R^2$ represents hydrogen or $C_{1-6}$ alkyl, $C_{2-6}$ alkenyl, $C_{2-6}$ alkynyl or $C_{3-6}$ cycloalkyl, (which latter four groups are optionally substituted by one or more halo atoms). In particular embodiments of the invention, $R^3$ in the compound of formula I represents —OH or, particularly, hydrogen.

In particular embodiments of the invention, $R^1$ represents hydrogen, $C_{1-4}$ alkyl (which latter group is optionally substituted by one or more halo atoms) or a suitable hydroxy protecting group (e.g. a benzoyl, acetyl, benzyl or toluenesulfonyl group); $R^2$ represents hydrogen or $C_{1-4}$ alkyl, (which latter group is optionally substituted by one or more halo atoms), or a suitable nitrogen protecting group, and $R^3$ represents hydrogen, —OH, $C_{1-4}$ alkyl, $C_{1-4}$ alkoxy (which latter two groups are optionally substituted by one or more halo atoms) or —$OR^p$ wherein $R^p$ is a suitable hydroxy protecting group (e.g. $R^p$ is benzoyl, acetyl, benzyl or toluenesulfonyl group).

In particular embodiments of the invention, $R^3$ in the compound of formula I represents hydrogen and $R^2$ represents methyl. In particular embodiments of the invention, $R^3$ represents hydrogen and $R^1$ represents hydrogen or methyl.

Particular compounds of formula I that may be mentioned in this respect are:

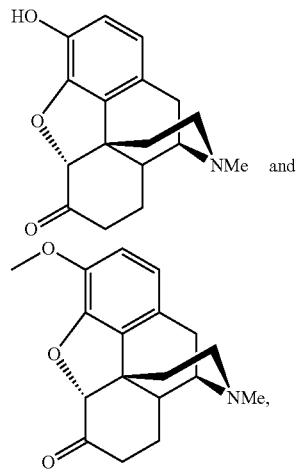

which may be prepared by redox isomerisation of an appropriate compound of formula II.

Additional compounds of formula I that may be mentioned in this respect include:

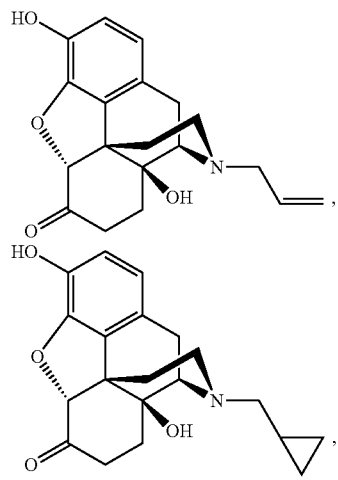

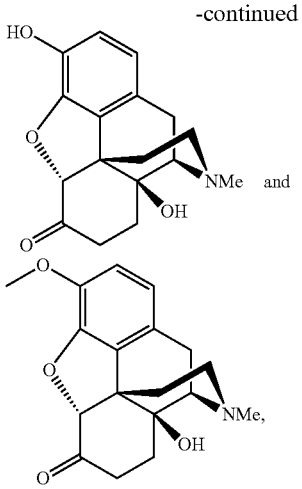

which may be prepared by redox isomerisation of an appropriate compound of formula II.

In a further embodiment of the invention there is provided a process for preparing a pharmaceutical formulation comprising a compound of formula I, or a salt thereof, as defined above, which process comprises the steps of:

(i) preparing a compound of formula I by contacting a compound of formula II, as defined above with a rhodium complex and an organic additive, as defined above;

(ii) optionally isolating and/or purifying the compound of formula I (or a salt thereof) obtained from that process; and (iii) bringing into association the compound of formula I so formed (or a salt thereof) with one or more pharmaceutically-acceptable excipients, adjuvants, diluents or carriers.

In a yet further embodiment of the invention there is provided a process for preparing a salt of a compound of formula I, as defined above, which process comprises the steps of:

(i) preparing a compound of formula I by contacting a compound of formula II, as defined above with a rhodium complex and an organic additive, as defined above;

(ii) optionally isolating and/or purifying the compound of formula I obtained from that process; and (iii) bringing into association the compound of formula I so formed with an acid (particularly an organic acid) under reaction conditions known to those skilled in the art, for example in the presence of a solvent (e.g. water, an alcohol (such as methanol or ethanol), acetonitrile, DMF, DMSO, or a mixture thereof) for example at or above room temperature (e.g. from room temperature to 105° C.), followed by removal of any solvent to afford the isolated salt.

Particular salts that may be mentioned in this respect include organic acid salts such as tartrate salts (e.g. bitartrate salts) and inorganic acid salts such as hydrohalide salts (e.g. hydrochloride salts).

The products of the process described herein may be purified via a purification step following the conversion of the compound of formula II to the compound of formula I, in which the purification step is a reduction step and/or a recrystallisation step. In particular embodiments, the process of the invention may include a first purification step that is a reduction step together with a second purification step that is a recrystallisation step. The reduction and recrystallisation steps may be performed in any order. In particular embodiments, the recrystallisation step is performed using the product obtained following the reduction step. In other embodiments, the recrystallisation step is performed without performing the reduction step.

In embodiments which involve a recrystallisation step, the recrystallisation step involves the dissolution of the compound of formula I (as obtained from the process of the invention) to obtain a solution of that compound in a solvent system (in particular, water, an organic solvent (e.g. an alcohol such as tert-butyl alcohol, a ketone, or an aromatic solvent such as toluene), or a mixture of water and an organic solvent, e.g. a mixture of water and an alcohol). The compound of formula I in the solvent system (e.g. in toluene or a mixture of water and tert-butyl alcohol) may be diluted with another solvent in order to promote the crystallisation. In particular embodiments, that other solvent is an ether, such as methyl tert-butyl ether, or an alcohol, such as tert-butyl alcohol.

In particular embodiments of the process involving a conversion step followed by a reduction step (either alone or in combination with a crystallisation step), the reduction step is carried out in the presence of a suitable reducing agent (for example, hydrogen) under conditions known to those skilled in the art, for example in the presence of a suitable catalyst (such as a palladium-based catalyst (e.g. palladium on carbon)). In more particular embodiments, the reduction step is conducted on the product obtained from the conversion step without isolating the products of the conversion step from the reaction mixture.

The purification step may be performed in order to reduce the levels of certain impurities present in the product of the conversion step. Such impurities include derivatives of compounds of formula I which derivatives contain one or more additional unsaturations, for example compounds in which the cyclohexanone ring portion contains an α,β-unsaturated ketone.

The processes described herein may be operated as a batch process or operated as a continuous process and may be conducted on any scale.

In another aspect of the invention, there is provided a hydrocodone product (e.g. hydrocodone or a salt thereof) comprising less than 50 ppm (such as less than 25 ppm, less than 10 ppm or less than 5 ppm) codeinone. In a particular embodiment, the hydrocodone product (e.g. hydrocodone or a salt thereof) comprises less than 10 ppm codeinone.

In embodiments of this aspect of the invention, at least a portion of the codeinone is derived from a transition metal mediated redox isomerisation of codeine to hydrocodone, for example a redox isomerisation process as defined herein.

The amount of α,β-unsaturated ketone derivative (e.g. codeinone) present in a given sample may be determined by any conventional method known to the person skilled in the art, such as LC-MS with SIR, or any method disclosed herein.

PARTICULAR EMBODIMENTS

Particular embodiments of the first aspect of the invention include the following.

(1) A process for the preparation of a compound of formula I,

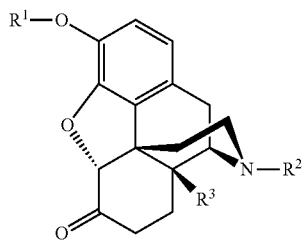

wherein:

$R^1$ represents hydrogen, $C_{1-18}$ alkyl, $C_{2-18}$ alkenyl, $C_{2-18}$ alkynyl or $C_{3-18}$ cycloalkyl, (which latter four groups are optionally substituted by one or more halo atoms) or a suitable hydroxy protecting group;

R² represents hydrogen or $C_{1-18}$ alkyl, $C_{2-18}$ alkenyl, $C_{2-18}$ alkynyl or $C_{3-18}$ cycloalkyl, (which latter four groups are optionally substituted by one or more halo atoms), or a suitable nitrogen protecting group; and R³ represents hydrogen, —OH, $C_{1-18}$ alkyl, $C_{1-18}$ alkoxy, $C_{2-18}$ alkenyl, $C_{2-18}$ alkynyl, $C_{3-18}$ cycloalkyl, (which latter five groups are optionally substituted by one or more halo atoms) or —OR$^p$ wherein R$^p$ is a suitable hydroxy protecting group;

which process comprises contacting a compound of formula II,

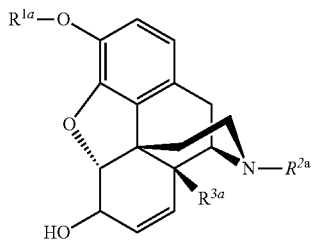

wherein $R^{1a}$, $R^{2a}$ and $R^{3a}$ are defined according to $R^1$, $R^2$ and $R^3$, respectively;

with:
(i) a rhodium complex; and
(ii) an organic additive selected from the group consisting of:
(a) alcohols of formula IIIa,

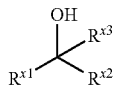

wherein $R^{x1}$, $R^{x2}$ and $R^{x3}$ independently represent hydrogen, a $C_{1-6}$ alkyl group, a $C_{2-6}$ alkenyl group, an aryl group or a heteroaryl group (which latter four groups may be optionally substituted by one or more halo atoms or $C_{1-4}$ alkyl groups); or any two of $R^{x1}$, $R^{x2}$ and $R^{x3}$ are linked together, along with the requisite carbon atom to which they are attached, to form a 4- to 8-membered cyclic alcohol, optionally containing one or more unsaturated bonds within the ring, and which ring is optionally substituted by one or more halo atoms or $C_{1-4}$ alkyl groups;

(b) ketones of formula IIIb,

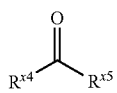

wherein $R^{x4}$ and $R^{x5}$ independently represent a $C_{1-4}$ alkyl group, a $C_{2-4}$ alkenyl group, an aryl group or a heteroaryl group (which four groups may be optionally substituted by one or more halo atoms or $C_{1-4}$ alkyl groups); or $R^{x4}$ and $R^{x5}$ are linked together, along with the requisite carbon atom to which they are attached, to form a 4- to 8-membered cyclic ketone, optionally containing one or more unsaturated bonds within the ring, and which ring is optionally substituted by one or more halo atoms or $C_{1-4}$ alkyl groups;

(c) ethers of formula IIIc,

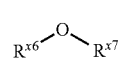

wherein $R^{x6}$ and $R^{x7}$ independently represent a $C_{1-4}$ alkyl group, or a $C_{2-4}$ alkenyl group (which groups may be optionally substituted by one or more halo atoms or $C_{1-4}$ alkyl groups); or $R^{x6}$ and $R^{x7}$ are linked together, along with the requisite oxygen atom to which they are attached, to form a 4- to 7-membered cyclic ether, optionally containing one or more unsaturated bonds within the ring, and which ring is optionally substituted by one or more halo atoms or $C_{1-4}$ alkyl groups; and (d) thioethers of formula IIId,

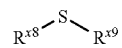

wherein $R^{x8}$ and $R^{x9}$ independently represent a $C_{1-4}$ alkyl group, or a $C_{2-4}$ alkenyl group (which groups may be optionally substituted by one or more halo atoms or $C_{1-4}$ alkyl groups); or $R^{x8}$ and $R^{x9}$ are linked together, along with the requisite sulfur atom to which they are attached, to form a 4- to 7-membered cyclic thioether, optionally containing one or more unsaturated bonds within the ring, and which ring is optionally substituted by one or more halo atoms or $C_{1-4}$ alkyl groups.

(2) A process according to Embodiment 1, wherein the rhodium complex is the main catalyst that is employed in the process of the invention.

(3) A process according to Embodiment 2, wherein a greater than 50% by weight, a greater than 75% by weight, or a greater than 90% by weight proportion of the catalyst in the process of the invention is a rhodium complex.

(4) A process according to Embodiment 3, wherein, the rhodium complex is employed as the sole catalyst in the process of the invention.

(5) A process according to any one of Embodiments 1 to 4, wherein the rhodium complex is a rhodium (I) complex.

(6) A process according to any one of Embodiments 1 to 5, wherein the solvent system is an alcohol, water, or a mixture of either an alcohol or water with one or more polar organic solvents.

(7) A process according to Embodiment 6, wherein the one or more polar organic solvents is selected from the group consisting of acetonitrile, methanol, ethanol, isopropanol, tert-butanol, ethylene glycol, dimethyl formamide, dimethyl sulfoxide, tetrahydrofuran, dimethyl ether, acetone, butanone, methyl ethyl ketone, diethyl ketone and methyl isobutyl ketone.

(8) A process according to Embodiments 6 or Embodiment 7, wherein the solvent system is a mixture of an alcohol and water.

(9) A process according to any one of Embodiments 6 to 8, wherein the solvent system consists predominantly of water or, consists almost exclusively of water.

(10) A process according to any one of Embodiments 6 to 9, wherein the solvent system consists of from 30% to 60% water by weight or by volume.

(11) A process according to Embodiments 10, wherein the solvent system consists of from 40% to 50% water by weight or by volume

(12) A process according to any one of Embodiments 6 to 9, wherein the solvent system consists of at least 30%, at least 40%, at least 50%, at least 60%, at least 70%, at least 80%, at least 90%, at least 95%, at least 96%, at least 97%, at least 98%, at least 99%, or about 100% water by weight or by volume.

(13) A process according to any one of Embodiments 1 to 12, wherein the solvent for the reaction is degassed prior to introduction of any of the starting materials.

(14) A process according to any one of Embodiments 1 to 13, wherein the amount of dissolved oxygen in the solvent prior to the introduction of the starting materials is below about 10 ppm, below about 1 ppm, or below about 0.5 ppm.

(15) A process according to any one of Embodiments 1 to 14, wherein the amount of the rhodium complex employed, relative to the compound of formula II, is at least 0.05 mol %, or from about 0.1 mol % to about 10 mol %.

(16) A process according to Embodiment 15, wherein the amount of the rhodium complex employed, relative to the compound of formula II, is from about 0.5 to about 5 mol % or about 1 mol %.

(17) A process according to any one of Embodiments 1 to 16, wherein the process is performed at elevated temperature.

(18) A process according to Embodiment 17, wherein the process is performed at a temperature of:
greater than about 60° C.;
greater than about 70° C.;
from about 65° C. to about 140° C.;
from about 75° C. to about 120° C.;
from about 90° C. to about 110° C.;
from about 95° C. to about 105° C.; or
about 100° C.

(19) A process according to any one of Embodiments 1 to 18, wherein the mixture including the compound of formula II and solvent is heated to about the particular temperature at which the process of the invention takes place, and then the rhodium complex is added at a rate such that the temperature of the process is maintained at about the particular temperature at which the process of the invention takes place.

(20) A process according to any one of Embodiments 1 to 19, wherein the rhodium complex is added over a sufficient period of time so as to maintain the temperature of the process of the invention at the particular ranges.

(21) A process according to any one of Embodiments 1 to 20, wherein the rhodium complex is added over a period of up to 30 minutes, up to 15 minutes, or up to about 10 minutes.

(22) A process according to any one of Embodiments 1 to 21, wherein the compound of formula I is obtained from the reaction mixture by filtration, or any other solid/liquid separation method known to the skilled person.

(23) A process according to any one of Embodiments 1 to 22, wherein the compound of formula I is further purified by crystallisation from a suitable solvent.

(24) A process according to any one of Embodiments 1 to 23, wherein the rhodium complex has a solubility in water of at least 0.01 g, at least 0.1 g, or at least 1 g per 100 g water at 20° C.

(25) A process according to any one of Embodiments 1 to 24, wherein the rhodium complex contains at least one water-soluble phosphine as a ligand.

(26) A process according to Embodiment 25, wherein the rhodium complex is pre-formed prior to addition to the compound of formula II.

(27) A process according to Embodiment 26, wherein, when the phosphine contains two or one phosphorus atoms capable of coordinating to rhodium, formation of the rhodium complex is achieved by mixing the water-soluble phosphine and a precursor rhodium complex in a molar ratio (of phospine:rhodium precursor) of at least 1:1, at least 1.5:1, from 1:1 to 3:1, or about 2:1.

(28) A process according to Embodiment 26 or Embodiment 27, wherein the formation of the rhodium complex is conducted in water, or a mixture of water with one or more polar organic solvents.

(29) A process according to Embodiment 28, wherein the one or more polar organic solvents is selected from the group consisting of methanol, ethanol, isopropanol, tert-butanol, dimethyl formamide, dimethyl sulfoxide acetone, butanone and methyl isobutyl ketone.

(30) A process according to Embodiment 28, wherein the formation of the rhodium complex is conducted in a solvent system which is predominantly of water or, consists almost exclusively of water.

(31) A process according to any one of Embodiments 1 to 18 or 22 to 25, wherein the rhodium complex is formed in the presence of the compound of formula II.

(32) A process according to Embodiment 31, wherein the rhodium complex is formed using at least one water-soluble phosphine ligand and a rhodium precursor complex.

(33) A process according to Embodiment 32, wherein the mixture containing the compound of formula II is heated to about the particular temperature at which the process of the invention should take place, following which the at least one water-soluble phosphine ligand and the rhodium precursor complex are added to the mixture containing the compound of formula II at a rate such that the temperature of the process is maintained at about the particular temperature at which the process of the invention takes place.

(34) A process according to Embodiment 33, wherein the at least one water-soluble phosphine ligand and the rhodium precursor complex are added to the mixture containing the compound of formula II over a period of up to about 30 minutes, up to about 15 minutes, or up to about 10 minutes.

(35) A process according to any one of Embodiments 32 to 34, wherein, when the water-soluble phosphine ligand contains two or one phosphorus atoms capable of coordinating to rhodium, formation of the rhodium complex is achieved by mixing the water-soluble phosphine and a precursor rhodium complex in a molar ratio (of phospine:rhodium precursor) of at least 1:1, at least 1.5:1, from 1:1 to 3:1, or about 2:1.

(36) A process according to any one of Embodiments 1 to 35, wherein the rhodium complex is a rhodium complex that is prepared from a water-soluble phosphine and either a precursor rhodium complex of formula IV, $$[Rh(diene)L_n]^+X^- \qquad \qquad IV$$

or a dimeric precursor rhodium complex of formula V, $$[Rh(diene)(Hal)]_2 \qquad \qquad V$$

wherein diene represents a diene ligand, X represents a halide or a non-coordinating anion, L represents a neutral ligand, n represents from 1 to 3, and Hal represents a halide or a hydroxide.

(37) A process according to Embodiment 36, wherein the diene ligand is selected from the group consisting of COD (1,5-cyclooctadiene), bicyclo[2,2,1]heptadiene and norbornadiene.

(38) A process according to Embodiment 36 or Embodiment 37, wherein the non-coordinating anion is selected from the group consisting of BARF, $SbF_6^-$, $BF_4^-$, $ClO_4^-$, $PF_6^-$, $HSO_4^-$, $H_2PO_4^-$, $CH_3CO_2^-$, $CF_3CO_2^-$, $CF_3SO_3^-$ and $PhCO_2^-$.

(39) A process according to any one of Embodiments 36 to 38, wherein L represents a ligand selected from the group consisting of acetonitrile, acetone, DMF, THF, DMSO or benzonitrile.

(40) A process according to any one of Embodiments 36 to 39, wherein n represents 2.

(41) A process according to any one of Embodiments 36 to 40, wherein Hal represents chloride.

(42) A process according to any one of Embodiments 36, 37 or 40 wherein the rhodium complex is prepared from a water-soluble phosphine and a dimeric precursor rhodium complex of formula V, and the rhodium complex is formed in the presence of a salt of the formula AY, wherein: wherein A represents an organic cation, such as triphenyl carbenium, or an inorganic cation selected from the group consisting of $Ag^+$, $Na^+$, $K^+$ or $Li^+$; and Y represents an anion selected from the group consisting of BARF, $SbF_6^-$, $BF_4^-$, $ClO_4^-$, $PF_6^-$, $HSO_4^-$, $H_2PO_4^-$, $CH_3CO_2^-$, $CF_3CO_2^-$, $CF_3SO_3^-$ and $PhCO_2^-$.

(43) A process according to any one of Embodiments 25 to 42, wherein the rhodium complex is prepared from a water-soluble phosphine and a precursor rhodium complex of formula IVA;

$$[Rh(diene)(CH_3CN)_2]^+X^- \quad\quad IVA$$

wherein diene represents a diene ligand and X represents a halide or a non-coordinating anion.

(44) A process according to Embodiment 43, wherein the diene ligand is selected from the group consisting of COD (1,5-cyclooctadiene), bicyclo[2,2,1]heptadiene and norbornadiene.

(45) A process according to Embodiment 43 or Embodiment 44, wherein the non-coordinating anion is selected from the group consisting of BARF, $SbF_6^-$, $BF_4$, $ClO_4^-$, $PF_6^-$, $HSO_4^-$, $H_2PO_4^-$, $CH_3CO_2^-$, $CF_3CO_2^-$, $CF_3SO_3^-$ and $PhCO_2^-$.

(46) A process according to Embodiment 45, wherein the rhodium complex is prepared from a water-soluble phosphine and $[Rh(COD)(CH_3CN)_2](BF_4)$.

(47) A process according to any one of Embodiments 25 to 30 and 32 to 46, wherein the water-soluble phosphine is a phosphine having a water-solubility of at least 0.1 g, at least 0.5 g, or at least 5 g per 100 g water at 20° C.

(48) A process according to any one of Embodiments 25 to 30 and 32 to 47, wherein the water-soluble phosphine is a phosphine in which each phosphorus atom of the phosphine is bound to three substituents via a carbon atom, wherein at least one of those three substituents bears at least one hydrophilic moiety.

(49) A process according to Embodiment 48, wherein each of the at least one hydrophilic moieties is independently selected from $-OR^v$, $-N(R^w)R^x$, $-C(O)-R^y$, $-S(O)_2OR^z$, and salts thereof, wherein each $R^v$ to $R^z$ independently represents hydrogen, or a $C_{1-4}$ alkyl, and wherein $R^w$ and $R^x$ groups attached to substituents on the same phosphorus atom may together form a $C_{1-3}$ alkylene chain.

(50) A process according to any one of Embodiments 25 to 30 and 32 to 49, wherein the phosphine is a compound of formula VI, $$P(R^4)(R^5)(R^6) \quad\quad VI$$

wherein each of $R^4$, $R^5$ and $R^6$ independently represents a $C_{1-6}$ alkyl or an aryl group, both of which groups may be optionally substituted by one or more groups selected from the list consisting of $-OR^{6a}$, $-SO_2OH$, $C(O)R^{7a}$, $-N(R^{8a})R^{9a}$, or a salt of $-SO_2OH$ or $-N(R^{8a})R^{9a}$; or any two of $R^4$, $R^5$ and $R^6$ may be linked together to form a 4- to 7- (e.g. 5- to 6-) membered ring, optionally containing one or more heteroatoms (for example, in addition to the phosphorus atom that is already present, one or more heteroatoms selected from oxygen, nitrogen and sulfur) and which ring is optionally substituted by one or more substituents selected from $-OR^{6b}$, $-SO_2OH$, $C(O)R^{7b}$, $-N(R^{8b})R^{9b}$, or a salt of $-SO_2OH$ or $-N(R^{8b})R^{9b}$;

or all three of $R^4$, $R^5$ and $R^6$ may be linked together to form a cage-like structure (e.g. having an adamantane-type skeleton) optionally containing one or more heteroatoms (for example, in addition to the phosphorus atom that is already present, one or more heteroatoms selected from oxygen, nitrogen and sulfur), and which cage-like structure is optionally substituted by one or more substituents selected from $-OR^{6c}$, $-SO_2OH$, $C(O)R^{7c}$, $-N(R^{8c})R^{9c}$, or a salt of $-SO_2OH$ or $-N(R^{8c})R^{9c}$;

wherein $R^{6a}$ $R^{6b}$, $R^{6c}$, $R^{7a}$, $R^{7b}$, $R^{7c}$, $R^{8a}$, $R^{8b}$, $R^{8c}$, $R^{9a}$ $R^{9b}$, and $R^{9c}$ are each independently selected from hydrogen, and $C_{1-4}$ alkyl.

(51) A process according to Embodiment 50, wherein the salt of $-SO_2OH$ is an alkali metal or an alkaline earth metal salt.

(52) A process according to Embodiment 51, wherein the salt of $-SO_2OH$ is a cesium, lithium, sodium or potassium salt.

(53) A process according to Embodiment 50 or Embodiment 52, wherein the acid addition salt of $-N(R^{8a})R^{9a}$, $-N(R^{8b})R^{9b}$ or $-N(R^{8c})R^{9c}$ is a salt of HCl, $H_2SO_4$, $H_3PO_4$ or an organic acid.

(54) A process according to Embodiment 53, wherein the organic acid is selected from the group consisting of acetic acid, methanesulfonic acid and toluenesulfonic acid derivatives (such as p-toluenesulfonic acid).

(55) A process according to any one of Embodiments 25 to 30 and 32 to 54, wherein the water-soluble phosphine is selected from the group consisting of:

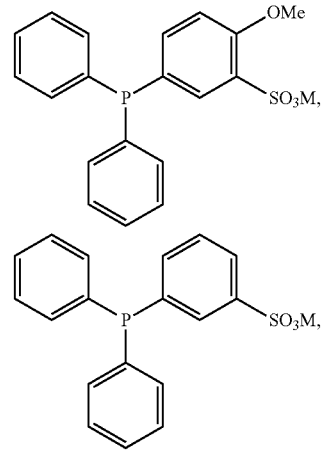

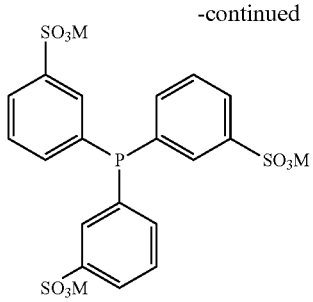

1,3,5-triaza-7-phosphaadamantane (PTA), and 1-methyl-1,3,5-triaza-7-phosphaadamantane, wherein M represents an alkali metal selected from potassium, sodium, lithium and cesium.

(56) A process according to Embodiment 37, wherein the water soluble phosphine is 1,3,5-triaza-7-phosphaadamantane (PTA) or a derivative thereof.

(57) A process according to any one of Embodiments 1 to 56, comprising an initial step of reacting a compound of formula IVA, as defined in Embodiment 43, with a compound of formula VI, as defined in Embodiment 50.

(58) A process according to Embodiment 57, wherein the initial step is performed prior to bringing the compound of formula II into contact with the resulting rhodium complex.

(59) A process according to Embodiment 57, wherein the initial step is performed in the presence of the compound of formula II.

(60) A process according to any one of Embodiments 1 to 59, wherein the rhodium complex is that formed by reacting [Rh(COD)(CH$_3$CN)$_2$](BF$_4$) with 1,3,5-triaza-7-phosphaadamantane.

(61) A process according to any one of Embodiments 1 to 60, wherein the organic additive is:
(a) a compound of formula IIIa, as defined in Embodiment 1, wherein $R^{x1}$, $R^{x2}$ and $R^{x3}$ each independently represents hydrogen, a C$_{1-4}$ alkyl group, a C$_{6-10}$ aryl group or a 5- to 10-membered heteroaryl group (which latter three groups may be optionally substituted by one or more halo atoms or C$_{1-4}$ alkyl groups);
(b) a compound of formula IIIb, as defined in Embodiment 1, wherein $R^{x4}$ and $R^{x5}$ each independently represents a C$_{1-4}$ alkyl group, a C$_{6-10}$ aryl group or a 5- to 10-membered heteroaryl group (which three groups may be optionally substituted by one or more halo atoms or C$_{1-4}$ alkyl groups);
(c) a compound of formula IIIc, as defined in Embodiment 1, wherein $R^{x6}$ and $R^{x7}$ each independently represents a C$_{1-2}$ alkyl group, or wherein $R^{x6}$ and $R^{x7}$ are linked together, along with the requisite oxygen atom to which they are attached, to form a 5- to 6-membered cyclic ether (which ring may be optionally substituted by one or more halo atoms or methyl groups); or
(d) a compound of formula IIId, as defined in Embodiment 1, wherein $R^{x8}$ and $R^{x9}$ each independently represents a C$_{3-4}$ alkyl group, or wherein $R^{x8}$ and $R^{x9}$ are linked together, along with the requisite sulfur atom to which they are attached, to form a 5- to 6-membered cyclic thioether (which ring may be optionally substituted by one or more halo atoms or methyl groups).

(62) A process according to any one of Embodiments 1 to 61, wherein the organic additive is:
(a) a compound of formula IIIa, as defined in Embodiment 1, wherein $R^{x1}$, $R^{x2}$ and $R^{x3}$ each independently represents hydrogen, a C$_{1-4}$ alkyl group, a C$_{6-10}$ aryl group or a 5- to 10-membered heteroaryl group (which latter three groups may be optionally substituted by one or more halo atoms or C$_{1-4}$ alkyl groups);
(b) a compound of formula IIIb, as defined in Embodiment 1, wherein $R^{x4}$ and $R^{x5}$ each independently represents a C$_{1-4}$ alkyl group, a C$_{6-10}$ aryl group or a 5- to 10-membered heteroaryl group (which three groups may be optionally substituted by one or more halo atoms or C$_{1-4}$ alkyl groups); or
(c) a compound of formula IIIc, as defined in Embodiment 1, wherein $R^{x6}$ and $R^{x7}$ each independently represents a C$_{1-2}$ alkyl group, or wherein $R^{x6}$ and $R^{x7}$ are linked together, along with the requisite oxygen atom to which they are attached, to form a 5- to 6-membered cyclic ether (which ring may be optionally substituted by one or more halo atoms or methyl groups).

(63) A process according to Embodiment 61, wherein the organic additive is selected from the group consisting of methanol, ethanol, isopropanol, n-propanol, n-butanol, sec-butanol, iso-butanol, tert-butanol, acetone, butanone methyl iso-butyl ketone, dimethyl ether, diethyl ether, tetrahydrofuran, methyl-tetrahydrofuran, dibutylsulfide, thiophene and tetrahydrothiophene.

(64) A process according to any one of Embodiments 61 to 63, wherein the organic additive is selected from the group consisting of methanol, ethanol, isopropanol, n-propanol, n-butanol, sec-butanol, iso-butanol, tert-butanol, acetone, butanone methyl iso-butyl ketone, dimethyl ether, diethyl ether, tetrahydrofuran and methyl-tetrahydrofuran.

(65) A process according to any one of Embodiments 61 to 64, wherein when the organic additive is a compound of formula IIIa, at least one of $R^{x7}$, $R^{x2}$ and $R^{x3}$ represents a C$_{1-4}$ alkyl group

(66) A process according to Embodiment 65, wherein the organic additive is acetone isopropanol or tert-butanol.

(67) A process according to any one of Embodiments 1 to 66, wherein the amount of organic additive that is present in the reaction is at least 0.5 equivalents, from 1 to 20 equivalents, from 2 to 10 equivalents, from 7 to 9 equivalents or about 8 equivalents, relative to the compound of formula II.

(68) A process according to any one of Embodiments 1 to 67, wherein the compound of formula II is brought into contact with the organic additive before the compound of formula II is brought into contact with the rhodium complex.

(69) A process according to Embodiment 68, wherein:
(i) the compound of formula II is provided in a suitable solvent system;
(ii) the rhodium complex is provided in an aqueous solvent system (e.g. a solvent system that consists predominantly of water);
(iii) the organic additive is added to the compound of formula II; and then
(iv) the solution comprising the rhodium complex is added to the mixture comprising the compound of formula II and the organic additive.

(70) A process according to Embodiment 69, wherein the organic additive is mixed together with the compound of formula II (and any associated solvents), and the mixture is then stirred for a sufficient duration (e.g. 15 minutes) before the rhodium complex is brought into contact with the mixture containing the compound of formula II and the organic additive.

(71) A process according to Embodiment 68, wherein:
(i) the compound of formula II is provided in a suitable solvent system;
(ii) the organic additive is added to the mixture of a compound of formula II and a solvent system; and then (iii) a water-soluble phosphine and a precursor rhodium complex are added (either sequentially or simultaneously) to the mixture comprising the compound of formula II, the organic additive and the solvent system.

(72) A process according to any one of Embodiments 1 to 71, wherein $R^1$ in the compound of formula I represents hydrogen, $C_{1-6}$ alkyl, $C_{2-6}$ alkenyl, $C_{2-6}$ alkynyl or $C_{3-6}$ cycloalkyl, (which latter four groups are optionally substituted by one or more halo atoms) or a suitable hydroxy protecting group.

(73) A process according to any one of Embodiments 1 to 71, wherein $R^3$ in the compound of formula I represents hydrogen and $R^1$ represents hydrogen or methyl.

(74) A process according to any one of Embodiments 1 to 71, wherein $R^2$ represents hydrogen or $C_{1-6}$ alkyl, $C_{2-6}$ alkenyl, $C_{2-6}$ alkynyl or $C_{3-6}$ cycloalkyl, (which latter four groups are optionally substituted by one or more halo atoms).

(75) A process according to any one of Embodiments 1 to 71, wherein $R^3$ in the compound of formula I represents hydrogen and $R^2$ in the compound of formula I represents methyl.

(76) A process according to any one of Embodiments 1 to 75, wherein the compound of formula I is selected from the group consisting of:

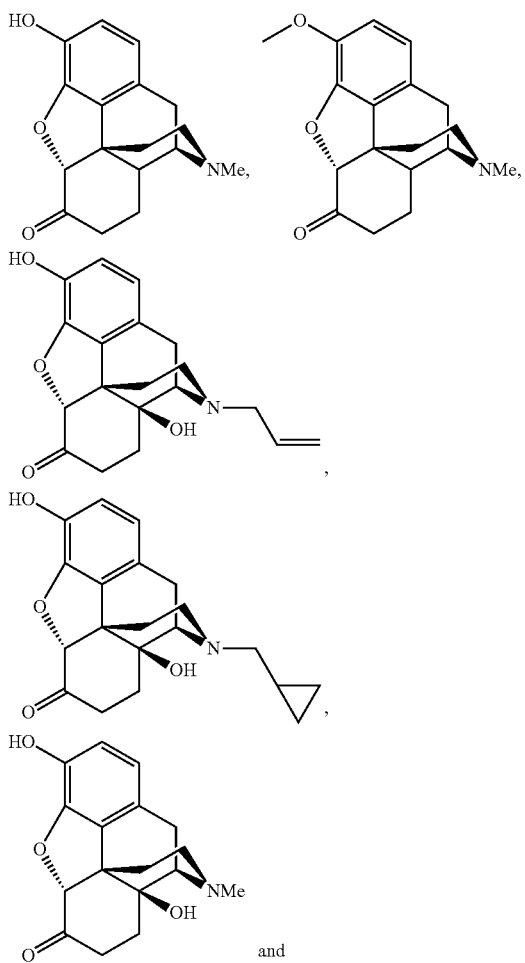

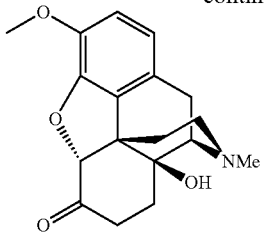

(77) A process according to any one of Embodiments 1 to 76, wherein the processes is operated as a batch process or operated as a continuous process.

(78) A process for preparing a salt of a compound of formula I, as defined in Embodiment 1, which process comprises the steps of:
 (i) preparing a compound of formula I by contacting a compound of formula II, as defined in Embodiment 1, with a rhodium complex and an organic additive, as defined in Embodiment 1, in accordance with the process as defined in any one of Embodiments 1 to 77;
 (ii) optionally isolating and/or purifying the compound of formula I obtained from that process; and
 (iii) bringing into association the compound of formula I so formed with an organic acid.

(79) A process according to Embodiment 78, wherein the salt of a compound of formula I is a bitartrate salt of that compound.

(80) A process according to Embodiment 78 or Embodiment 79, wherein the process is conducted in the presence of a solvent selected from the group consisting of water, methanol, ethanol, isopropanol, tert-butanol, ethylene glycol, acetonitrile, DMF, DMSO, tetrahydrofuran, dimethyl ether, acetone, butanone, methyl ethyl ketone, diethyl ketone, methyl isobutyl ketone, and mixtures thereof, followed by removal of the solvent to afford the isolated salt.

(81) A process according to any one of Embodiments 78 to 80, wherein the process is conducted at or above room temperature.

(82) A process according to any one of Embodiments 78 to 81, wherein the process is conducted at from room temperature to 105° C.

(83) A process according to any one of Embodiments 1 to 82, wherein following the conversion of the compound of formula II to the compound of formula I, the process further comprises a reduction step.

(84) A process according to Embodiment 83, wherein the reduction step is carried out in the presence of hydrogen.

(85) A process according to Embodiment 84, wherein the reduction step is also carried out in the presence of a palladium-based catalyst.

(86) A process according to any one of Embodiments 83 to 85, wherein the reduction step is conducted on the product obtained from the conversion step without isolating the products of the conversion step from the reaction mixture.

(87) A process according to any one of Embodiments 1 to 82, wherein following the conversion of the compound of formula II to the compound of formula I, the process further comprises a recrystallisation step.

(88) A process for preparing a pharmaceutical formulation comprising a compound of formula I, or a salt thereof, as defined in Embodiment 1, which process comprises the steps of:
 (i) preparing a compound of formula I by contacting a compound of formula II, as defined in Embodiment 1, with a rhodium complex and an organic additive, as defined in Embodiment 1, in accordance with the process as defined in any one of Embodiments 1 to 87;

(ii) optionally isolating and/or purifying the compound of formula I (or a salt thereof) obtained from that process; and (iii) bringing into association the compound of formula I so formed (or a salt thereof) with one or more pharmaceutically-acceptable excipients, adjuvants, diluents or carriers.

In general, the processes described herein, may have the advantage that the compounds of formula I may be produced in a manner that utilises fewer reagents and/or solvents, and/or requires fewer reaction steps (e.g. distinct/separate reaction steps) compared to processes disclosed in the prior art. Processes described herein may also have the advantage that fewer undesired by-products (resultant of undesired side reactions) may be produced, for example, by-products that may be toxic or otherwise dangerous to work with, e.g. corrosive, and achieves high levels of conversion whilst avoiding the need to include difficult and/or expensive purification steps. The processes may also be more economical or efficient than those described in the prior art.

The processes of the invention may also have the advantage that the compound of formula I is produced in higher yield, in higher purity, in higher selectivity, in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art. Furthermore, there may be several environmental benefits of the process of the invention.

The use of an aqueous solvent system (e.g. wherein water is the sole or predominant solvent) in the process of the invention provides an economically beneficial process as the solvent is relatively inexpensive. In addition, by using a metal-based catalyst that is soluble in the solvent system, the metal can not only be easily separated (e.g. by filtration), it also has a reduced effect on the quality of the product which is filtered off once the reaction is complete.

Relatively high yields of conversion for the processes of the invention may be obtained using relatively low levels of catalyst (rhodium complex), in particular such as from about 0.05 mol % to about 0.3 mol %. Advantageously, the process of the invention may be performed to take advantage of higher temperatures (in order to optimise conversion, and yield) but not excessively high temperatures (in order to prevention side-reactions, by products and unwanted degradation). In particular, it is desirable to reduce the amount of residual metal catalyst that remains as the catalyst is often expensive and may also be toxic and/or harmful to the environment.

The following examples are merely illustrative examples of the processes of the invention described herein.

All equipment, reagents and solvents used were standard laboratory equipment, e.g. glassware, heating apparatus and HPLC apparatus.

EXAMPLES

Analytical Method

The analytical method described below was used to determine the amount of codeinone in samples of hydrocodone base and hydrocodone bitartrate hemi(pentahydrate).
Materials and Equipment
  Acetonitrile, HPLC grade
  Methanol, HPLC grade
  Water (Milli-Q)
  Ammonium formate (p.a. grade)
  Ammonium hydroxide (p.a. grade)
  Waters UPLC equipped with gradient pump, column thermostat and MS detector (TQD) or equivalent
  Column: Waters Acquity BEH C18, 2.1×50 mm 1.7 μm or equivalent
  Analytical balance
  Reference standard: Codeinone
  Samples of hydrocodone base and/or hydrocodone bitartrate
Analytical Conditions
  UPLC operating parameters

| Flow rate | | 0.4 ml/min | |
|---|---|---|---|
| Gradient | Time (min) | Mobile phase A (%) | Mobile phase B (%) |
| | 0 | 90 | 10 |
| | 3 | 60 | 40 |
| | 5 | 55 | 45 |
| | 8 | 10 | 90 |
| | 10 | 10 | 90 |
| Injection volume | 1 μL | | |
| Needle wash | 3 sec post-wash | | |
| Solvent for needle wash | 25/25/25/25 MeOH/ACN/2-propanol/Water | | |
| Temperature | 30° C. | | |
| Max pressure | 1000 bar | | |

MS operating parameters

| Ionization | Electrospray |
|---|---|
| Polarity | Positive |
| Cone voltage | 46 (V) |
| Capillary voltage | 0.60 kV |
| Extractor voltage | 3 (V) |
| RF lens | 0.1 (V) |
| Source temperature | 150° C. |
| Cone gas flow | 30 L/h |
| Desolvation gas flow | 800 L/h |
| Desolvation temperature | 400° C. |
| Dwell time | 0.04 sec |
| Span | 0.2 Da |
| Signal detection | Single ion recording of m/z 298.4 |

Mobile phase preparation A:
10 mM Ammonium formate in water, pH 9.5
Mobile phase preparation B:
MeOH
Diluent:
50/50 ACN/H$_2$O
Codeinone stock standard solution
Codeinone 0.2 mg/mL in diluent.
Codeinone Working Standard Solutions
Prepare a series of standard solutions (n=5) in the range corresponding to the expected amount of codeinone in the sample solutions.
Hydrocodone Sample Solutions
Hydrocodone free base 1.2 mg/mL in diluent.
Hydrocodone bitartrate hemi(pentahydrate) 2 mg/mL in diluent.
Calculations
Analyze the working standard solutions and plot the response of codeinone versus codeinone concentration to establish a linear relationship. Measure the response of codeinone in the sample and interpolate to find the concentration of codeinone in the samples.

Peak identification is done by comparing the chromatogram of the sample solution with that of the working standard solution, verifying that the observed molecular weight match that of the reference standard.

For hydrocodone base samples, calculate the concentration (in ppm) of codeinone in the sample by formula (1):

$$\text{Assay(ppm)} = \frac{A_{xS} \times 1000000}{f_x \times c_{xS}} \quad (1)$$

The calculation gives the amount of codeinone related to hydrocodone free base in ppm.

For hydrocodone bitartrate hemi(pentahydrate) samples, calculate the concentration (in ppm) of codeinone in the sample by formula (2):

$$\text{Assay(ppm)} = \frac{A_{xS} \times 1000000}{f_x \times c_{xS}} \times (\text{MW-}BT/\text{MW-Base}) \quad (2)$$

The calculation gives the amount of codeinone related to hydrocodone free base in ppm.

| | |
|---|---|
| $f_x$ | response factor of codeinone in reference solution (area/conc) |
| $c_{xR}$ | concentration of codeinone in reference solution (mg/mL) |
| $c_{xS}$ | concentration of sample solution (mg/mL) |
| $A_{xR}$ | area of codeinone in reference chromatogram |
| $A_{xS}$ | area of codeinone in sample chromatogram |
| MW-BT | molecular weight of bitartrate hemi (pentahydrate) |
| MW-Base | molecular weight of hydrocodone free base |

Example 1

Preparation of Hydrocodone

The reaction was carried out under nitrogen using standard techniques in a sealed tube.

Preparation of the Catalyst:

1,3,5-Triaza-7-phosphaadamantane (5.4 mg, 0.03 mmol) and [Rh(COD)(CH$_3$CN)$_2$]BF$_4$ (6.4 mg, 0.017 mmol) were dissolved in 10 mL of distilled and degassed water some minutes prior to use.

Preparation of Hydrocodone:

Codeine (1 g, 3.34 mmol) was suspended in 5 mL of distilled and degassed water. The suspension was heated to 100° C. and 2 mL of the catalyst solution (0.1 mol %) was added. The reaction was stirred vigorously at this temperature for 24 hrs, cooled to room temperature, then filtered and washed with water (3×5 mL). The white-grey solid was dried giving hydrocodone (824 mg, 82.4%) with >99 area % purity.

Example 2

Preparation of Hydromorphone

The reaction was carried out under nitrogen using standard techniques in a sealed tube.

Preparation of the Catalyst:

1,3,5-Triaza-7-phosphaadamantane (17 mg, 0.10 mmol) and [Rh(COD)(CH$_3$CN)$_2$]BF$_4$ (20 mg, 0.05 mmol) were dissolved in 7 mL of distilled and degassed water and used immediately after preparation.

Preparation of Hydromorphone:

Morphine CPS (1 g, 92% w/w, 3.22 mmol) was added to the solution of the catalyst. The suspension was stirred vigorously at 100° C. for 17 hrs, then cooled to room temperature, filtered and washed with water (3×5 mL). The white-grey solid was dried giving hydromorphone (718 mg, 78%) with >99 area % purity.

Example 3

Catalyst Loading and Temperature

Redox isomerisation experiments using codeine were carried out with different catalyst loadings and temperatures (Table 1).

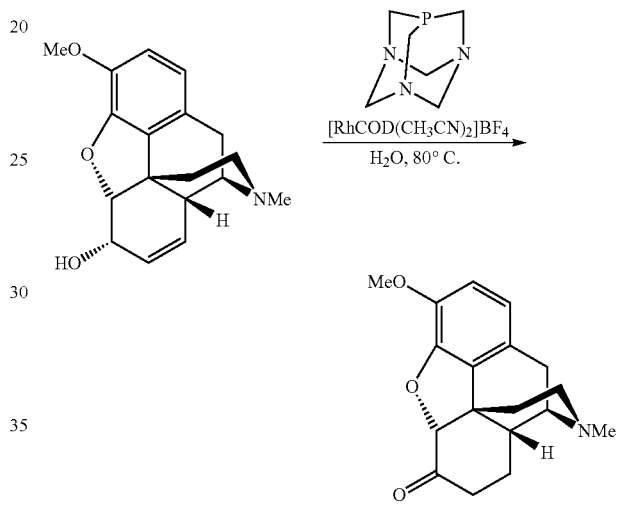

TABLE 1

| Entry | Time (h) | Temperature (° C.) | Catalyst (mol %) | Phosphine (mol %) | Conversion |
|---|---|---|---|---|---|
| 1 | 2 | 80 | 5 | 10 | 93% |
| 2 | 3 | 80 | 1 | 2 | 94% |
| 3 | 12 | 80 | 0.1 | 0.2 | 87% |
| 4 | 21 | 70 | 0.05 | 0.1 | 30% |
| 5 | 21 | 100 | 0.05 | 0.1 | 93% |
| 6 | 24 | 130 | 0.05 | 0.1 | 98% |
| 7 | 24 | 100 | 0.1 | 0.2 | >99% |

The data show that effective levels of conversion are achieved at catalyst levels down as low as 0.05 mol % (Entry 6). Increased conversion is seen at increased temperatures (Entries 4 and 5).

Example 4

Rhodium/Phosphine Ratio

Redox isomerisation experiments using codeine were conducted in which the rhodium/phosphine ratio was varied (Table 2). Aqueous solutions of the precursor rhodium complex and phosphine were added sequentially to the reaction mixture containing codeine.

TABLE 2

| Entry | Catalyst (mol %) | Phosphine (mol %) | Conversion |
|---|---|---|---|
| 1 | 0.05 | 0.1 | 44% |
| 2 | 0.05 | 0.075 | 19% |
| 3 | 0.05 | 0.05 | 12% |

The best result was when the rhodium to phosphine ratio was 1:2.

Example 5

Catalyst Loading

Redox isomerisation experiments using morphine were carried out with different catalyst loadings (Table 3).

TABLE 3

| Entry | Time (h) | Temperature (° C.) | Catalyst (mol %) | Phosphine (mol %) | Conversion |
|---|---|---|---|---|---|
| 1 | 2 | 100 | 5 | 10 | 99% |
| 2 | 20 | 100 | 0.5 | 1 | 86% |
| 3 | 24 | 100 | 0.5 | 1 | 97% |
| 4 | 21 | 100 | 1 | 2 | >99%[a] |

[a]Isolated yield of hydromorphone was 75%.

Example 6

Phosphine Ligands

Redox isomerisation experiments were conducted using codeine with different water-soluble phosphines (Scheme 1).

Scheme 1

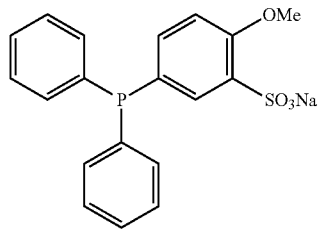

82% conversion

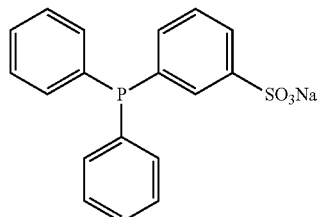

83% conversion

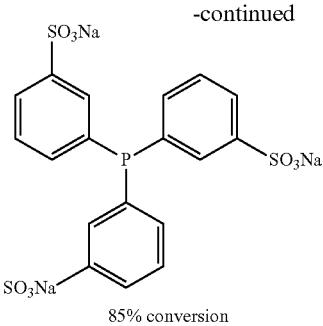

85% conversion

Conversions were similar to that obtained using PTA (≈90%).

Example 7

Redox Isomerisation of Cyclohex-2-enol in the Presence of Isopropanol

Redox isomerisation experiments were conducted using cyclohex-2-enol in the presence of isopropanol. Cyclohex-2-enol (1.0 g, 10.18 mmol) was added to a solution of $[Rh(COD)(CH_3CN)_2]BF_4$ (0.1 mol %) and PTA (0.2 mol %) in 7 mL water and heated at 100° C. for 1 hr. Isopropanol (6 equivalents) was added to the solution of the catalyst before addition of the cyclohex-2-enol, or to the cyclohex-2-enol before addition to the catalyst solution (Table 4).

TABLE 4

|  | Cyclohexanone | Cyclohex-2-enone | Cyclohex-2-enol |
|---|---|---|---|
| No additive | 52.2% | 1.7% | 44.7% |
| IPA added to catalyst | 51.7% | 1.1% | 45.7% |
| IPA added to cyclohexenol | 95.5% | 0.53% | 2.4% |

When the reaction was carried out without an additive, 52% cyclohexanone was observed along with 1.7% of the enone. A similar result was seen when the isopropanol was added to the catalyst solution, although the level of the enone decreased slightly to 1.1%. When the isopropanol was added to the cyclohexenol solution, the conversion to cyclohexanone increased and the level of the enone decreased to 0.53%.

Example 8

Redox Isomerisation of Codeine CPS to Hydrocodone (Using IPA)

Codeine CPS (with a codeine content of 700 g, 2.34 mol) was charged to a reactor followed by water (1967 mL) and IPA (843 g, 1073 mL). The resulting mixture was heated to 37° C. and degassed three times via a vacuum/nitrogen cycle.

The catalyst solution was prepared by degassing water (10 mL) three times via a vacuum/argon cycle. [Rh(COD)(CH$_3$CN)$_2$]BF$_4$ (880 mg, 2.34 mol) and 1,3,5-Triaza-phosphaadamantane (0.735 g, 4.68 mol) were added and an extra vacuum/argon cycle applied. The resulting solution was stirred under argon for 10 minutes then added to the reaction mixture. The reaction mixture was heated to reflux (~85° C.) for 22 hrs.

The reaction mixture was cooled to 5° C. and stirred at this temperature for 1 hr. The precipitate was filtered off and washed with water (2×1 L). The product was dried to give 628.38 g hydrocodone. HPLC analysis: hydrocodone—>99%; codeinone—1300 ppm.

Example 9

Redox Isomerisation of Codeine CPS to Hydrocodone (Using $^t$BuOH)

A mixture of Codeine CPS (975.0 g; having a codeine content of 881.4 g, 2.9 mol), water (2270 mL) and tert-butanol (2304 mL) was placed in a reactor, degassed, and heated to reflux (~82° C.).

A mixture of 1,3,5-triaza-phosphaadamantane (0.92 g, 5.9 mmol) and [Rh(COD)(CH$_3$CN)$_2$]BF$_4$ (1.12 g, 2.9 mmol) was placed in a separate reactor. Degassed water (50 mL) was added and the mixture stirred under nitrogen. The resulting solution was added to the codeine mixture at reflux and stirred for 16 hrs at this temperature. A solution of 50% NaOH in water (29.4 mL) was added, and approximately 40% of the solvent was removed by distillation. The resulting mixture was cooled to 5° C. over 4 hrs and filtered. The solid was washed with an aqueous NaOH solution (1763 mL) followed by water (2×1763 mL). The final product was dried to give 806.5 g hydrocodone. HPLC analysis: hydrocodone—>99%, codeinone—less than 10 ppm.

Example 10

Redox Isomerisation (Using tBuOH with In Situ Rh-Complex Formation)

A mixture of Codeine CPS (29.7 g; having a codeine content of 26.0 g, 86.9 mmol), purified water (62 mL) and tert-butanol (as 59.4 g, 73.9 mL of a 10% aqueous tert-butyl alcohol solution) was placed in a reactor, degassed, and heated to ~50° C. 1,3,5-Triaza-phosphaadamantane (27.3 mg, 0.174 mmol) and [Rh(COD)(CH$_3$CN)$_2$]BF$_4$ (33.0 mg, 0.086.9 mmol) were added to the reactor and the resulting mixture was degassed and heated to ~82° C. and stirred under nitrogen for 16 hrs.

After the reaction was completed, the solvent level was reduced by distillation, and the reaction mixture was cooled to ~10° C. over 5 hrs. The precipitate was recovered by filtration and washed with water (2×78 mL). The resulting product was dried to give 23.7 g hydrocodone. HPLC analysis: hydrocodone: >99%; codeinone: <10 ppm.

Example 11

Redox Isomerisation of Codeine CPS to Hydrocodone (Using Acetone)

A mixture of Codeine CPS (16.53 g; having a codeine content of 15.0 g, 50 mmol), water (38.7 mL) and acetone (39.2 mL) was placed in a reactor, degassed, and heated to reflux (~82° C.).

A mixture of 1,3,5-triaza-phosphaadamantane (15.7 mg, 0.1 mmol) and [Rh(COD)(CH$_3$CN)$_2$]BF$_4$ (19 mg, 0.05 mmol) was placed in a separate reactor. Degassed water (0.9 mL) was added and the mixture stirred under nitrogen. The resulting solution was added to the codeine mixture at reflux and stirred for 16 hrs at this temperature. A solution of 50% NaOH in water (0.5 mL) was added, and approximately 40% of the solvent was removed by distillation. The resulting mixture was cooled to 5° C. over 4 hrs and filtered. The solid was washed with an aqueous NaOH solution (30 mL) followed by water (2×30 mL). The final product was dried to give 13.73 g hydrocodone. HPLC analysis: hydrocodone—>99%, codeinone—0.32%.

The invention claimed is:
1. A process for the preparation of a compound of formula I,

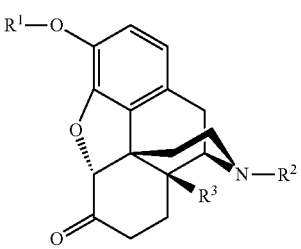

wherein:
R$^1$ represents hydrogen, C$_{1-18}$ alkyl, C$_{2-18}$ alkenyl, C$_{2-18}$ alkynyl or C$_{3-18}$ cycloalkyl, (which latter four groups are optionally substituted by one or more halo atoms) or a suitable hydroxy protecting group;
R$^2$ represents hydrogen or C$_{1-18}$ alkyl, C$_{2-18}$ alkenyl, C$_{2-18}$ alkynyl or C$_{3-18}$ cycloalkyl, (which latter four groups are optionally substituted by one or more halo atoms), or a suitable nitrogen protecting group; and
R$^3$ represents hydrogen, —OH, C$_{1-18}$ alkyl, C$_{1-18}$ alkoxy, C$_{2-18}$ alkenyl, C$_{2-18}$ alkynyl, C$_{3-18}$ cycloalkyl, (which latter five groups are optionally substituted by one or more halo atoms) or —OR$^P$ wherein R$^P$ is a suitable hydroxy protecting group;
which process comprises contacting a compound of formula II,

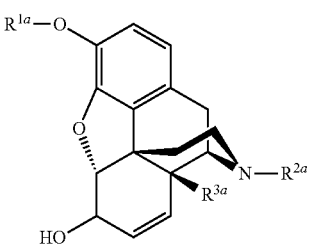

wherein R$^{1a}$, R$^{2a}$ and R$^{3a}$ are defined according to R$^1$, R$^2$ and R$^3$, respectively,
with:
(i) a rhodium complex; and
(ii) an organic additive selected from the group consisting of:
(a) alcohols of formula IIIa,

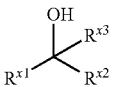

wherein R$^{x1}$, R$^{x2}$ and R$^{x3}$ independently represent hydrogen, a C$_{1-6}$ alkyl group, a C$_{2-6}$ alkenyl group, an aryl group or a heteroaryl group (which latter four groups may be optionally substituted by one or more halo atoms or C$_{1-4}$ alkyl groups); or any two of $R^{x1}$, $R^{x2}$ and $R^{x3}$ are linked together, along with the requisite carbon atom to which they are attached, to form a 4- to 8-membered cyclic alcohol, optionally containing one or more unsaturated bonds within the ring, and which ring is optionally substituted by one or more halo atoms or $C_{1-4}$ alkyl groups;

(b) ketones of formula IIIb,

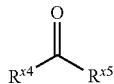
IIIb wherein $R^{x4}$ and $R^{x5}$ independently represent a $C_{1-4}$ alkyl group, a $C_{2-4}$ alkenyl group, an aryl group or a heteroaryl group (which four groups may be optionally substituted by one or more halo atoms or $C_{1-4}$ alkyl groups); or $R^{x4}$ and $R^{x5}$ are linked together, along with the requisite carbon atom to which they are attached, to form a 4- to 8-membered cyclic ketone, optionally containing one or more unsaturated bonds within the ring, and which ring is optionally substituted by one or more halo atoms or $C_{1-4}$ alkyl groups;

(c) ethers of formula IIIc,

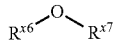
IIIc wherein $R^{x6}$ and $R^{x7}$ independently represent a $C_{1-4}$ alkyl group, or a $C_{2-4}$ alkenyl group (which groups may be optionally substituted by one or more halo atoms or $C_{1-4}$ alkyl groups); or $R^{x6}$ and $R^{x7}$ are linked together, along with the requisite oxygen atom to which they are attached, to form a 4- to 7-membered cyclic ether, optionally containing one or more unsaturated bonds within the ring, and which ring is optionally substituted by one or more halo atoms or $C_{1-4}$ alkyl groups; and (d) thioethers of formula IIId,

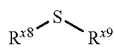
IIId wherein $R^{x8}$ and $R^{x9}$ independently represent a $C_{1-4}$ alkyl group, or a $C_{2-4}$ alkenyl group (which groups may be optionally substituted by one or more halo atoms or $C_{1-4}$ alkyl groups); or $R^{x8}$ and $R^{x9}$ are linked together, along with the requisite sulfur atom to which they are attached, to form a 4- to 7-membered cyclic thioether, optionally containing one or more unsaturated bonds within the ring, and which ring is optionally substituted by one or more halo atoms or $C_{1-4}$ alkyl groups, wherein the rhodium complex is water-soluble, and prepared from a water-soluble phosphine and a precursor rhodium complex of formula IV,

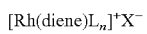
IV or a dimer of formula V,

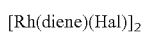
V wherein diene represents a diene ligand, X represents an anion, L represents a neutral ligand, n represents 1 to 3, and Hal represents a halide or a hydroxide, and wherein, when the rhodium complex is prepared from the water-soluble phosphine and the dimer of formula V, the rhodium complex is formed in the presence of a salt of formula AY, wherein A represents an organic or inorganic cation, and Y represents a non-coordinating anion, and wherein the conversion of the compound of formula II to the compound of formula I is performed in an aqueous solvent system.

2. The process as claimed in claim 1, wherein $R^3$ represents hydrogen and $R^2$ represents methyl.

3. The process as claimed in claim 1, wherein $R^3$ represents hydrogen, $R^2$ represents methyl and $R^1$ represents hydrogen or methyl.

4. The process as claimed in claim 1, wherein the organic additive is:
(a) a compound of formula IIIa, as defined in claim 1, wherein $R^{x1}$, $R^{x2}$ and $R^{x3}$ each independently represents hydrogen, a $C_{1-4}$ alkyl group, a $C_{6-10}$ aryl group or a 5- to 10-membered heteroaryl group (which latter three groups may be optionally substituted by one or more halo atoms or $C_{1-4}$ alkyl groups);
(b) a compound of formula IIIb, as defined in claim 1, wherein $R^{x4}$ and $R^{x5}$ each independently represents a $C_{1-4}$ alkyl group, a $C_{6-10}$ aryl group or a 5- to 10-membered heteroaryl group (which three groups may be optionally substituted by one or more halo atoms or $C_{1-4}$ alkyl groups);
(c) a compound of formula IIIc, as defined in claim 1, wherein $R^{x6}$ and $R^{x7}$ are linked together, along with the requisite oxygen atom to which they are attached, to form a 5- to 6-membered cyclic ether (which ring may be optionally substituted by one or more halo atoms or methyl groups); or
(d) a compound of formula IIId, as defined in claim 1, wherein $R^{x8}$ and $R^{x9}$ independently represent a $C_{1-4}$ alkyl group, or a $C_{2-4}$ alkenyl group (which groups may be optionally substituted by one or more halo atoms or $C_{1-4}$ alkyl groups).

5. The process as claimed in claim 4, wherein the organic additive is tert-butanol, isopropanol or acetone.

6. The process as claimed in claim 1, wherein the compound of formula II is brought into contact with the organic additive before the compound of formula II is brought into contact with the rhodium complex.

7. The process as claimed in claim 1, wherein:
(i) the compound of formula II is provided in the aqueous solvent system;
(ii) the organic additive is added to the mixture of a compound of formula II and the aqueous solvent system; and then
(iii) the water-soluble phosphine and the precursor rhodium complex are added to the mixture comprising the compound of formula II, the organic additive and the aqueous solvent system.

8. The process as claimed in claim 1, wherein the organic additive is added in an amount of from 1 to 20 equivalents relative to the amount of the compound of formula II.

9. The process as claimed in claim 1, wherein the aqueous solvent comprises from 30% to 60% by weight of water.

10. The process as claimed in claim 1, wherein the process is performed at a temperature of greater than about 60° C.

11. The process as claimed in claim 1, wherein:
(i) the rhodium complex is pre-formed from the water-soluble phosphine and the precursor rhodium complex prior to addition to the compound of formula II; or
(ii) the rhodium complex is formed from the water-soluble phosphine and the precursor rhodium complex in the presence of the compound of formula II.

12. The process as claimed in claim 11, wherein the precursor rhodium complex is a compound of formula IVA;

   IVA wherein diene represents a diene ligand, and X represents a suitable anion.

13. The process as claimed in claim 11, wherein the water-soluble phosphine is a compound of formula VI,

   VI wherein each of $R^4$, $R^5$ and $R^6$ independently represents a $C_{1-6}$ alkyl or an aryl group, both of which groups may be optionally substituted by one or more groups selected from the list consisting of —$OR^{6a}$, —$SO_2OH$, $C(O)R^{7a}$, —$N(R^{8a})R^{9a}$, or a salt of —$SO_2OH$ or —$N(R^{8a})R^{9a}$;

or any two of $R^4$, $R^5$ and $R^6$ may be linked together to form a 4- to 7- (e.g. 5- to 6-) membered ring, optionally containing one or more heteroatoms (for example, in addition to the phosphorus atom that is already present, one or more heteroatoms selected from oxygen, nitrogen and sulfur) and which ring is optionally substituted by one or more substituents selected from —$OR^{6b}$, —$SO_2OH$, $C(O)R^{7b}$, —$N(R^{8b})R^{9b}$, or a salt of —$SO_2OH$ or —$N(R^{8b})R^{9b}$;

or all three of $R^4$, $R^5$ and $R^6$ may be linked together to form a cage-like structure (e.g. having an adamantane-type skeleton) optionally containing one or more heteroatoms (for example, in addition to the phosphorus atom that is already present, one or more heteroatoms selected from oxygen, nitrogen and sulfur), and which cage-like structure is optionally substituted by one or more substituents selected from —$OR^{6c}$, —$SO_2OH$, $C(O)R^{7c}$, —$N(R^{8c})R^{9c}$, or a salt of —$SO_2OH$ or —$N(R^{8c})R^{9c}$;

wherein $R^{6a}$, $R^{6b}$, $R^{6c}$, $R^{7a}$, $R^{7b}$, $R^{7c}$, $R^{8a}$, $R^{8b}$, $R^{8c}$, $R^{9a}$ $R^{9b}$, and $R^{9c}$ are each independently selected from hydrogen, and $C_{1-4}$ alkyl.

14. The process as claimed in claim 1, wherein the rhodium complex is a complex formed by reacting [Rh(COD)(CH$_3$CN)$_2$](BF$_4$) with 1,3,5-triaza-7-phosphaadamantane, wherein COD represents 1,5-cyclooctadiene.

15. A process for the preparation of a compound of formula I,

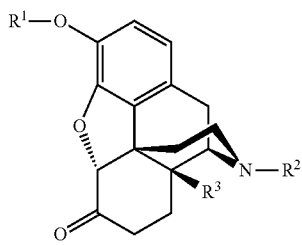   I wherein:
$R^1$ represents hydrogen, $C_{1-4}$ alkyl (which latter group is optionally substituted by one or more halo atoms) or a suitable hydroxy protecting group;

$R^2$ represents hydrogen or $C_{1-4}$ alkyl, (which latter group is optionally substituted by one or more halo atoms), or a suitable nitrogen protecting group; and $R^3$ represents hydrogen, —OH, $C_{1-4}$ alkyl, $C_{1-4}$ alkoxy (which latter two groups are optionally substituted by one or more halo atoms) or —$OR^P$ wherein $R^P$ is a suitable hydroxy protecting group;

which process comprises contacting a compound of formula II,

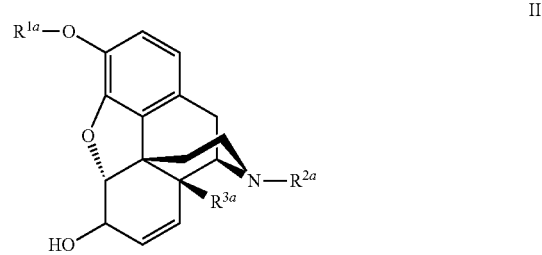   II wherein $R^{1a}$, $R^{2a}$ and $R^{3a}$ are defined according to $R^1$, $R^2$ and $R^3$, respectively;
with:
(i) a rhodium complex, and
(ii) an organic additive that is:
(a) a compound of formula IIIa, as defined in claim 1, wherein $R^{x1}$, $R^{x2}$ and $R^{x3}$ each independently represents hydrogen, a $C_{1-4}$ alkyl group, a $C_{6-10}$ aryl group or a 5- to 10-membered heteroaryl (which latter three groups may be optionally substituted by one or more halo atoms or $C_{1-4}$ alkyl groups);
(b) a compound of formula IIIb, as defined in claim 1, wherein $R^{x4}$ and $R^{x5}$ each independently represents a $C_{1-4}$ alkyl group, a $C_{6-10}$ aryl group or a 5- to 10-membered heteroaryl group (which three groups may be optionally substituted by one or more halo atoms or $C_{1-4}$ alkyl groups);
(c) a compound of formula IIIc, as defined in claim 1, wherein $R^{x6}$ and $R^{x7}$ are linked together, along with the requisite oxygen atom to which they are attached, to form a 5- to 6-membered cyclic ether (which ring may be optionally substituted by one or more halo atoms or methyl groups); or
(d) a compound of formula IIId, as defined in claim 1, wherein $R^{x8}$ and $R^{x9}$ independently represent a $C_{1-4}$ alkyl group, or a $C_{2-4}$ alkenyl group (which groups may be optionally substituted by one or more halo atoms or $C_{1-4}$ alkyl groups);
wherein the organic additive is present in an amount of from 1 to 20 equivalents relative to the compound of formula II, and the conversion of the compound of formula II to the compound of formula I is performed in an aqueous solvent system,
wherein the rhodium complex is water-soluble, and prepared from a water-soluble phosphine and a precursor rhodium complex of formula IV,

   IV or a dimer of formula V,

   V wherein diene represents a diene ligand, X represents an anion, L represents a neutral ligand, n represents 1 to 3, and Hal represents a halide or a hydroxide, and wherein, when the rhodium complex is prepared from the water-soluble phosphine and the dimer of formula V, the rhodium complex is formed in the presence of a salt of formula AY, wherein A represents an organic or inorganic cation, and Y represents a non-coordinating anion.

16. A process for the preparation of a compound of formula I,

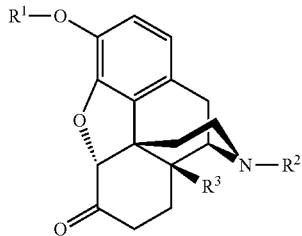

wherein:
$R^1$ represents hydrogen or methyl;
$R^2$ represents methyl;
$R^3$ represents hydrogen;
which process comprises contacting a compound of formula II,

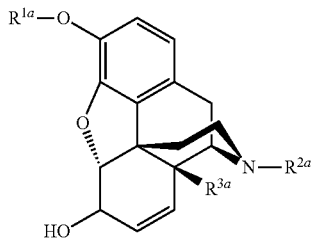

wherein $R^{1a}$, $R^{2a}$ and $R^{3a}$ are defined according to $R^1$, $R^2$ and $R^3$, respectively;
with a rhodium complex, and tert-butanol,
wherein the rhodium complex is prepared from a water-soluble phosphine and $[Rh(COD)(CH_3CN)_2](BF_4)$, and the conversion of the compound of formula II to the compound of formula I is performed in an aqueous solvent system that comprises from 30% to 60% water by weight or by volume, wherein COD represents 1,5-cyclooctadiene.

17. The process as claimed in claim 1, which comprises a further processing step following the conversion of the compound of formula II to the compound of formula I, wherein the further processing step is a recrystallisation step.

18. The process as claimed in claim 1, which comprises the additional step of crystallisation of the compound of formula I from a solvent system.

19. A process for preparing a salt of a compound of formula I, as defined in claim 1, which process comprises the steps of:
(i) preparing a compound of formula I in accordance with the process as defined in claim 1;
(ii) optionally isolating and/or purifying the compound of formula I obtained from that process; and
(iii) bringing into association the compound of formula I so formed with an organic acid.

20. A process for preparing a pharmaceutical formulation comprising a compound of formula I, or a salt thereof, as defined in claim 1, which process is characterised in that it includes as a process step a process as claimed in claim 1 followed by bringing into association the compound of formula I (or a salt thereof) so formed, with one or more pharmaceutically-acceptable excipients, adjuvants, diluents or carriers.

21. The process as claimed in claim 1, wherein the aqueous solvent comprises at least 20% by weight of water.

22. The process as claimed in claim 1, wherein A is triphenyl carbenium, $Ag^+$, $Na^+$, $K^+$ or $Li^+$; and Y is tetrakis (polyfluoroaryl)borate, $SbF_6^-$, $BF_4^-$, $ClO_4^-$, $PF_6^-$, $HSO_4^-$, $H_2PO_4^-$, $CH_3CO_2^-$, $CF_3CO_2^-$, $CF_3SO_3^-$ or $PhCO_2^-$.

23. The process as claimed in claim 1, wherein diene is 1,5-cyclooctadiene, bicyclo[2,2,1]heptadiene or norbornadiene, X is halide, tetrakis(polyfluoroaryl)borate, $SbF_6^-$, $BF_4^-$, $ClO_4^-$, $PF_6^-$, $HSO_4^-$, $H_2PO_4^-$, $CH_3CO_2^-$, $CF_3CO_2^-$, $CF_3SO_3^-$ or $PhCO_2^-$, and L is acetonitrile, acetone, dimethyl formamide, tetrahydrofuran, dimethyl sulfoxide or benzonitrile.

* * * * *